United States Patent
Bunch et al.

(10) Patent No.: US 9,044,143 B2
(45) Date of Patent: Jun. 2, 2015

(54) FLUIDIC ESOPHAGEAL HEAT SENSORS

(71) Applicants: T. Jared Bunch, South Jordan, UT (US); Troy J. Orr, Draper, UT (US)

(72) Inventors: T. Jared Bunch, South Jordan, UT (US); Troy J. Orr, Draper, UT (US)

(73) Assignee: Intermountain Invention Management, LLC, Salt Lake City, UT (US)

( * ) Notice: Subject to any disclaimer, the term of this patent is extended or adjusted under 35 U.S.C. 154(b) by 138 days.

(21) Appl. No.: 13/763,697

(22) Filed: Feb. 10, 2013

(65) Prior Publication Data

US 2013/0211283 A1    Aug. 15, 2013

Related U.S. Application Data

(60) Provisional application No. 61/597,291, filed on Feb. 10, 2012.

(51) Int. Cl.

| A61B 18/04 | (2006.01) |
|---|---|
| A61B 5/01 | (2006.01) |
| A61B 18/02 | (2006.01) |
| A61B 18/18 | (2006.01) |
| A61B 18/12 | (2006.01) |
| A61B 5/00 | (2006.01) |

(Continued)

(52) U.S. Cl.
CPC . *A61B 5/01* (2013.01); *A61B 5/687* (2013.01); *A61B 5/4836* (2013.01); *A61B 18/02* (2013.01); *A61B 18/1815* (2013.01); *A61B 18/12* (2013.01); *A61B 18/1492* (2013.01); *A61B 2018/00023* (2013.01); *A61B 2018/00041* (2013.01); *A61B 2018/00357* (2013.01); *A61B 2018/00577* (2013.01); *A61B 2018/00791* (2013.01); *A61B 2018/0212* (2013.01); *A61B 2018/1861* (2013.01); *A61B 5/6853* (2013.01); *A61B 2562/0271* (2013.01)

(58) Field of Classification Search
CPC ............ A61B 5/00; A61B 5/01; A61B 5/687; A61B 5/4836; A61B 18/02; A61B 2018/02
USPC ......................................................... 606/32
See application file for complete search history.

(56) References Cited

U.S. PATENT DOCUMENTS

| 3,898,431 A | 8/1975 | House et al. |
|---|---|---|
| 6,053,912 A | 4/2000 | Panescu et al. |
| 6,438,400 B1 | 8/2002 | Beard et al. |

(Continued)

FOREIGN PATENT DOCUMENTS

| WO | WO2013/120042 | 8/2012 |
|---|---|---|
| WO | WO2013/120043 | 8/2012 |

OTHER PUBLICATIONS

International Search Report and Written Opinion dated Feb. 10, 2013 for PCT/US2013/025471.

(Continued)

*Primary Examiner* — Robert N Wieland
(74) *Attorney, Agent, or Firm* — Stoel Rives LLP

(57) ABSTRACT

Heat sensors can be positioned within the esophagus of a patient so as to monitor temperature changes during ablation procedures in the heart. Some heat sensors can include one or more fluid passageways that define an extended heat sensing region capable of detecting a change in the local temperature. Some heat sensors can be conformable to an inner surface of the esophageal wall to maintain contact therewith or to be in close proximity thereto.

24 Claims, 24 Drawing Sheets

(51) Int. Cl.
*A61B 18/14* (2006.01)
*A61B 18/00* (2006.01)

(56) References Cited

U.S. PATENT DOCUMENTS

| | | |
|---|---|---|
| 2003/0009165 A1 | 1/2003 | Edwards et al. |
| 2003/0088299 A1* | 5/2003 | Magers et al. ............... 607/104 |
| 2004/0260328 A1 | 12/2004 | Zvuloni et al. |
| 2004/0267339 A1* | 12/2004 | Yon et al. ..................... 607/105 |
| 2007/0049999 A1 | 3/2007 | Esch et al. |
| 2007/0270793 A1 | 11/2007 | Lattouf |
| 2009/0131930 A1 | 5/2009 | Gelbart et al. |
| 2010/0121159 A1 | 5/2010 | Burnett et al. |
| 2010/0179537 A1 | 7/2010 | Rashidi |
| 2010/0204560 A1 | 8/2010 | Salahieh et al. |
| 2010/0298895 A1 | 11/2010 | Ghaffari et al. |
| 2011/0264075 A1 | 10/2011 | Leung et al. |
| 2012/0323089 A1 | 12/2012 | Feer et al. |
| 2013/0030425 A1 | 1/2013 | Stewart et al. |
| 2013/0211282 A1 | 8/2013 | Bunch et al. |

OTHER PUBLICATIONS

International Search Report and Written Opinion dated Feb. 10, 2013 for PCT/US2013/025472.
Office Action dated Jan. 26, 2015 in U.S. Appl. No. 13/763,696.

* cited by examiner

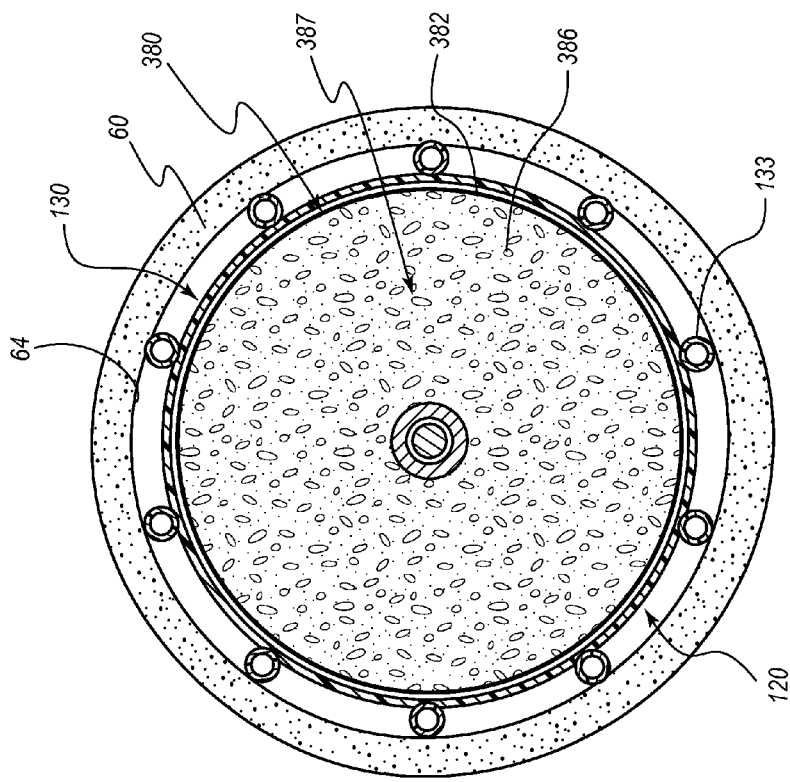
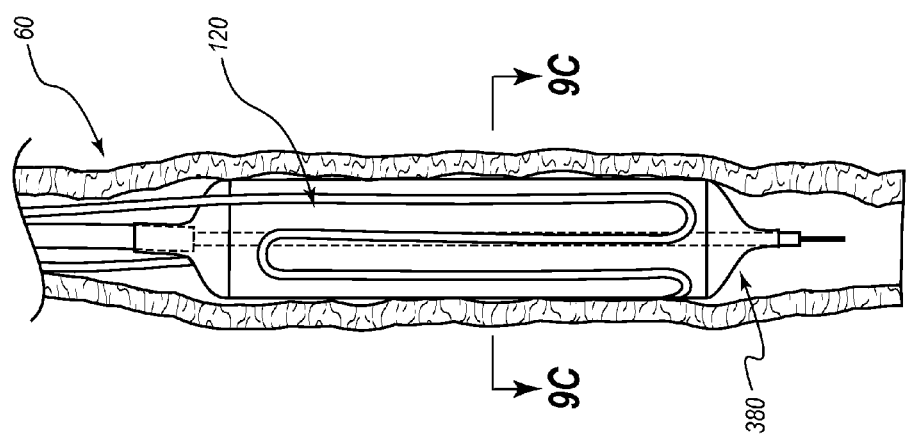

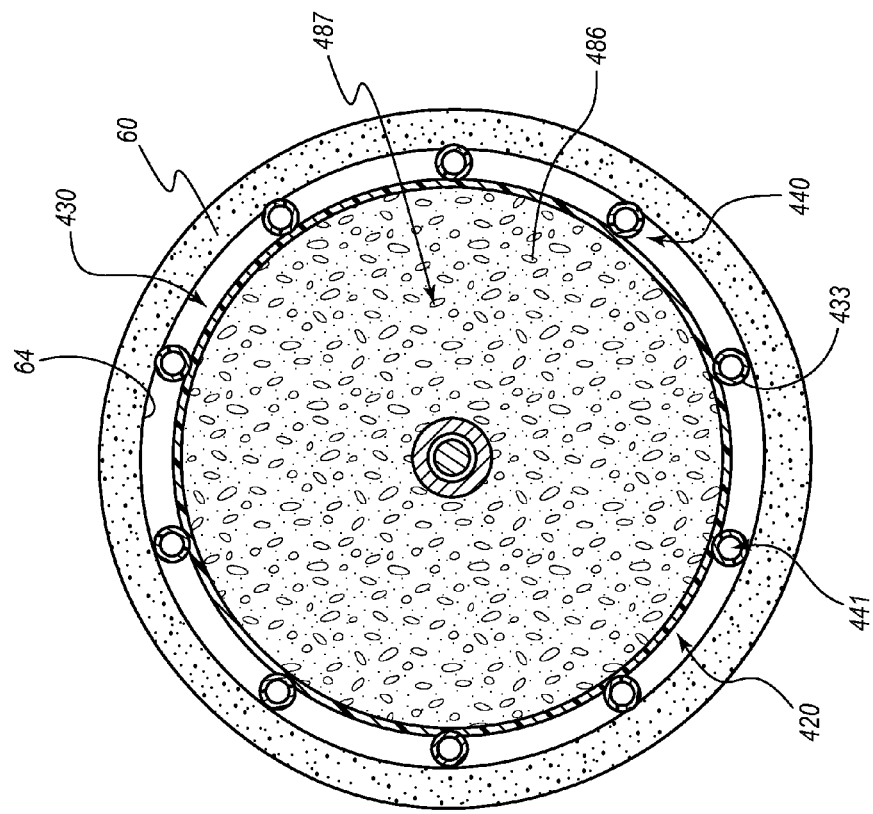
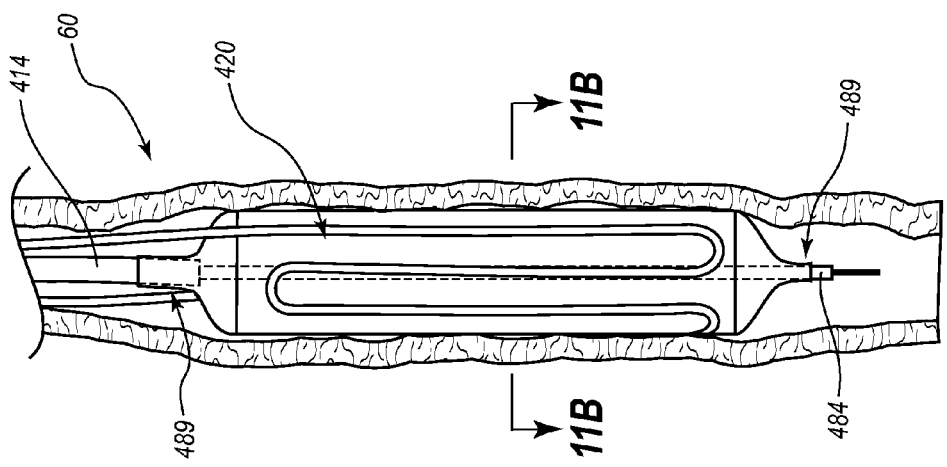
FIG. 11B
FIG. 11A

FLUIDIC ESOPHAGEAL HEAT SENSORS

CROSS-REFERENCE TO RELATED APPLICATIONS

This application claims the benefit under 35 U.S.C. §119(e) of U.S. Provisional Patent Application No. 61/597,291, titled ESOPHAGEAL TEMPERATURE SENSOR, filed on Feb. 10, 2012, the entire contents of which are hereby incorporated by reference herein.

TECHNICAL FIELD

The present disclosure relates generally to medical heat sensors, and relates more particularly to heat sensors that can be deployed within the esophagus.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 9B is an enlarged view of the heat sensor and a portion of the inflation system within the esophagus of the patient taken along the view line 9B-9B in FIG. 9A;

FIG. 9C is a cross-sectional view of the heat sensor and the portion of the inflation system within the esophagus of the patient taken along the view line 9C-9C in FIG. 9B;

FIG. 11A is an elevation view of another embodiment of a heat sensor within the esophagus of a patient (shown in cross-section) during an inflation stage in which inflation fluid is pressurized to bring the heat sensor into close proximity to the inner wall of the esophagus;

FIG. 11B is a cross-sectional view of the heat sensor of FIG. 11A taken along the view line 11B-11B;

DETAILED DESCRIPTION

Figure 1:
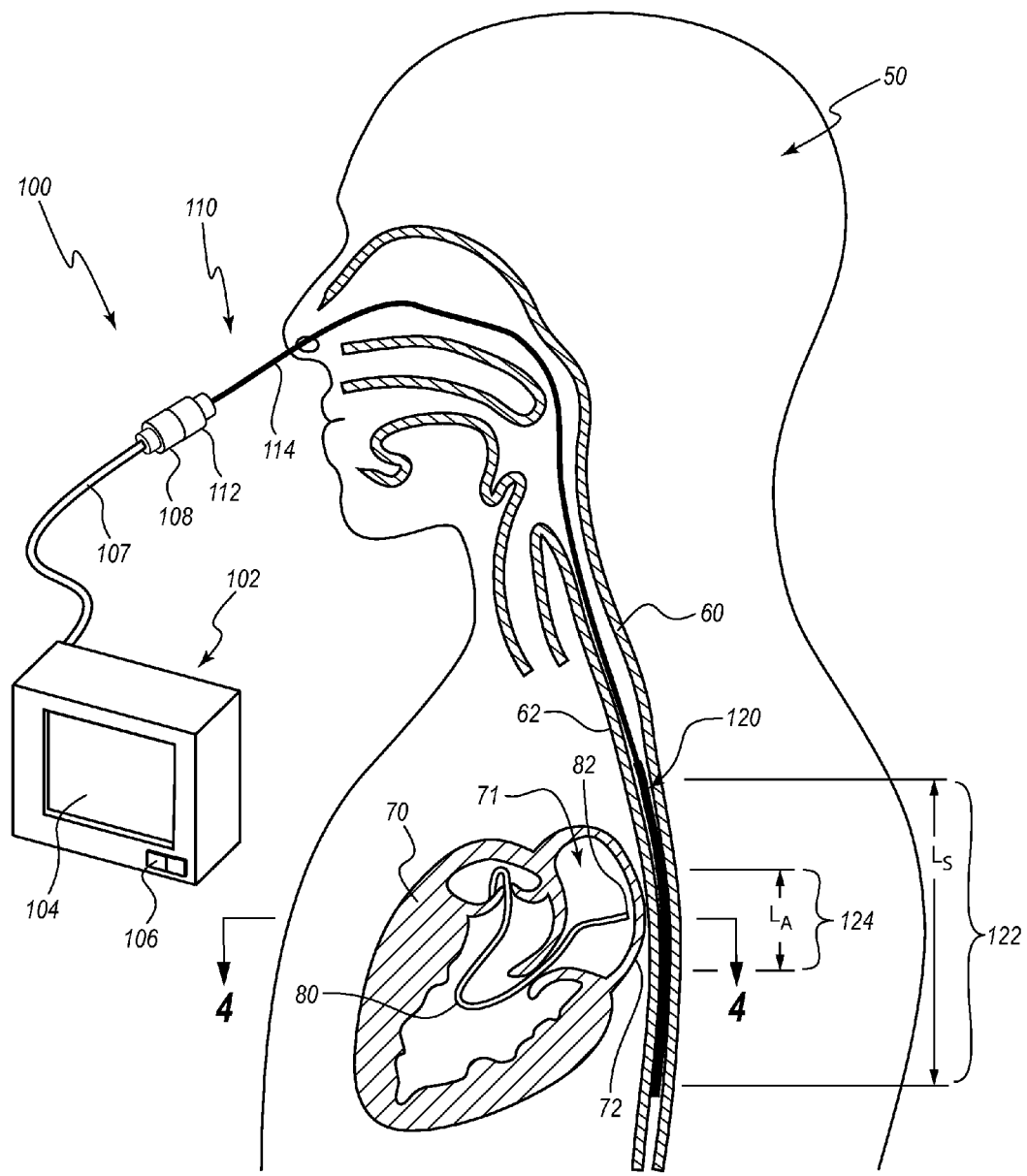
FIG. 1 is a perspective view of an embodiment of a heat sensing system, wherein an embodiment of a heat sensor is shown positioned within a patient that is schematically depicted in cross-section, and wherein the heat sensor is in use during a cardiac ablation procedure.

Atrial fibrillation ("AF") is a heart disease in which electrical impulses that are normally generated by the sinoatrial node are overwhelmed by disorganized electrical activity in the atrial tissue, leading to an irregular conduction of impulses to the ventricles that generate the heartbeat. The result is an irregular heartbeat, which may be intermittent or continuous. In human populations, AF-induced irregular heartbeat is a significant source of stroke, heart failure, disability, and death.

A number of surgical options are available for treating AF. One approach is widely known as the Cox-Maze III procedure. In this procedure, the left atrial appendage is excised, and a series of incisions and/or cryolesions are arranged in a maze-like pattern in the atria. The incisions encircle and isolate the pulmonary veins. The resulting scars block the abnormal electrical pathways, improving normal signal transmission and restoring regular heart rhythm. While its success rate is relatively good, the Cox-Maze III procedure and variations thereof are complex open-heart surgeries, that can require cardiopulmonary bypass, median sternotomy, and endocardial incisions that require suturing of the atria. The risks of complications from Cox-Maze III can be significant.

Some techniques use heating or cooling sources to create impulse-blocking lesions on the heart by ablation, rather than incision. Other ablation techniques have been developed that use one or more of incisions, cryoablation, microwave, and unipolar or bipolar radiofrequency ("RF") energy to create the pattern of lesions achieved in the original Cox-Maze III procedure. For example, certain unipolar RF techniques have been used for ablation in endocardial procedures. Endocardial ablation can result in perforation of surrounding organs, due mainly to the difficulty of achieving consistent burn penetration.

Some of the more serious complications that can arise from any of the foregoing ablation procedures are those caused by time-dependent, deep heating through excessive heat transfer. A perforation of the atrial wall due to excessive heating can cause permanent structural damage to the heart, or to the heart and to surrounding tissue. For example, excessive heat transmitted by RF energy or microwaves can permeate the thin wall of the left atrium and fuse it with the esophagus, forming a fistula between the two organs. This creates a pathway into the heart for bacteria from the esophagus, posing a significant risk of infection, endocarditis, systemic sepsis, and mediastinitus outside the heart and in the heart itself. Accordingly, it can be desirable to monitor the temperature of the esophagus wall, or stated otherwise, to detect changes to the temperature (e.g., heating or cooling), during certain ablation procedures. Such monitoring can assist in early detection of overheating (or, in the case of cryoablation, overcooling) of the atrial wall and/or the esophageal wall, which likewise can prevent or reduce damage to the heart and/or esophagus.

Disclosed herein are various embodiments of heat sensing systems and heat sensors that can be used during AF treatments so as to ameliorate or eliminate one or more of problems discussed above. In various embodiments, the heat sensors can be situated at a position within the esophagus that is nearest the tip of an ablation device, which tip may be at a position within the heart of the patient. Some heat sensors can have an extended region capable of detecting a rise (or, in the case of cryoablation, a fall) in the local temperature at any position within that region. In some embodiments, the heat sensors can be configured to conform to an inner surface of the esophageal wall so as to maintain contact therewith and/or so as to be in close proximity to the ablation device without altering the natural conformation of the esophagus. Such arrangements can permit monitoring of the temperature of the esophageal wall without substantially deforming the wall; for example, without moving the esophageal wall into closer proximity to the ablation site at the atrial wall. In other or further embodiments, the esophageal wall may be brought into proximity with (e.g., into contact with) the sensor after the sensor has been positioned within the esophagus at a desired location. In certain of such embodiments, the esophagus can be collapsed against the sensor, and may even be collapsed in a manner so as to provide additional spacing between the ablation tip and the esophagus. Other embodiments are also disclosed. The foregoing advantages and/or other advantages of various embodiments will be evident from the disclosure herein.

FIG. 1 is a perspective view of an embodiment of a heat sensing system 100 that can be used in any suitable medical procedure. In the illustrated embodiment, the heat sensing system 100 is configured for use during an AF ablation procedure. For example, a patient 50 can undergo any suitable ablation procedure of the left atrium wall 72 of the heart 70 of the patient. Any suitable ablation tool 70 can be introduced into the left atrium 71, and an ablation tip 72 can be positioned at or near the atrium wall 72. The ablation tip 72 can be used to create impulse-blocking lesions in the atrium wall 72 in any suitable manner, such as those described above. For example, in various embodiments, the tip 72 is configured to impart microwave and/or RF energy to the atrium wall 72 so as to heat specific regions of the wall, and/or to conduct cryoablation of the atrium wall 72 so as to cool specific regions of the wall. The ablation tool 70 may also be referred to as a heat source or, for cryoablation procedures, as a cooling source.

The wall 62 of the esophagus 60 of the patient can be in close proximity to the atrial wall 72 during the ablation procedure. Accordingly, in some instances, the procedure can heat and/or cool the esophageal wall 62. As previously discussed, it may be desirable to avoid significant temperature changes at the esophageal wall 62 so as to minimize or prevent tissue injury and/or perforation of the wall 62 and/or formation of a fistula between the esophagus 60 and the heart 70.

Accordingly, the heat sensing system 100 can be configured to monitor a temperature at the wall 62 of the esophagus 60 and/or to monitor changes in the temperature of the wall 62. In cases of microwave ablation or RF ablation, for example, the temperature of the wall 62 may increase, whereas in cases of cryoablation, the temperature may decrease. It should be appreciated that apparatus and methods disclosed herein with respect to the esophagus 60 and the ablation tool 70 that is used outside of the esophagus 60 may be used in other contexts. For example, various embodiments may be configured for use in other anatomical vessels, where heating (or cooling) occurs outside of the vessels or at the vessel walls. Moreover, various embodiments may be used with other mammalian esophagi and/or other anatomical vessels.

The heat sensing system 100 can include a monitor or controller 102, which may include one or more buttons or actuators 106 that are configured to effect one or more operations, such as navigating through menus, making selections, or otherwise providing commands. The controller 102 can include a display 104 that is configured to display information in a visually perceivable format. For example, the display 104 can comprise a screen of any suitable variety, including those presently known and those yet to be devised. For example, the screen 104 can comprise a liquid crystal display (LCD) panel. In some embodiments, the screen 104 can be configured to receive information or otherwise interact with a medical practitioner. For example, the screen 104 can comprise a touch screen. The controller 102 can be coupled with a heat sensing assembly 110, so as to communicate therewith, in any suitable manner.

In the illustrated embodiment, the controller 102 and the heat sensing assembly 110 are coupled with each other via a connection line 107 having a connector 108. As further discussed below, the controller 102 can include one or more fluid control devices, which may be incorporated into a single unit with the controller 102. In other embodiments, the controller 102 and the fluidic control devices may be housed in separate housings and may merely communicate with each other electronically or in any other suitable fashion. In some embodiments, the connection line 107 may include multiple lumens or conduits through which fluid can be held and/or conducted or transported.

Various procedures discussed herein, such as monitoring of temperature, or detection of heating or cooling, can be accomplished via the monitor or controller 102. In some embodiments, the controller 102 can comprise a general-purpose or special-purpose computer, or some other electronic device, and at least a portion of the procedures may be embodied in machine-executable instructions therein. In other embodiments, at least a portion of the procedures (e.g., various steps or stages thereof) may be performed by hardware components that include specific logic for performing the steps or by a combination of hardware, software, and/or firmware.

The heat sensing assembly 110 can include a heat sensor 120 that is configured to be positioned within the esophagus 60 of the patient 50. The heat sensor 120 can be positioned at an end of a catheter 114, which may include one or more conduits or lumens to permit fluid communication between the controller 102 and/or any fluidic devices controlled thereby and the heat sensor 120. In some embodiments, the catheter 114 may include a connector 112 that is configured to interface with the connector 108. The heat sensor 120 can be configured to detect a temperature and/or a change in temperature (e.g., heating or cooling), as further discussed below.

As shown in FIG. 1, in some embodiments, the heat sensor 120 may define a heat sensing zone or sensing region 122 that extends along a sensing length $L_S$. The sensing length $L_S$ may be significantly greater than a length $L_A$ of a temperature alteration region or zone 124, which may also be referred to as a heat alteration region or zone. Having a heat sensing region 122 that exceeds a length of the temperature alteration zone 124 that may have an altered temperature (e.g., increased or decreased temperature) during an ablation procedure can aid in ensuring that the heat sensor 120 detects the temperature change, or stated otherwise, detects heating or cooling. Moreover, in some instances, the heat sensor 120 can be positioned within the esophagus 60 such that a portion of the length $L_S$ is distal to the position at which the ablation tip 72 is closest to the esophagus 60 and another portion of the length $L_S$ is proximal to the position at which the ablation tip 72 is closest to the esophagus 60, such as the position at which the atrial wall 72 is closest to the esophagus 60. In various embodiments, the length $L_A$ can be within a range of from about 2 centimeters to about 7 centimeters, and the length $L_S$ can be greater than the length $L_A$ and within a range of from about 4 centimeters to about 10 centimeters. In other or further embodiments, the length $L_S$ can be no less than about 2, 4, 6, 7, or 10 centimeters, no greater than about 4, 6, 7, or 10 centimeters, or within a range of from about 2 to 10, 4 to 10, or 4 to 7 centimeters. In some embodiments, the sensing length $L_S$ can be roughly the same length as a maximum length of the heart 70 of the patient 50. Other sensing lengths $L_S$ and temperature alteration lengths $L_A$ are also possible.

The temperature alteration zone 124 can extend through a volume of space at an interior of the esophagus 60. For example, in some embodiments, the temperature alteration zone 124 may be substantially conical, frustoconical, or cylindrical, depending on the manner in which heat propagates through an interior of the esophagus 60 due to a localized heat source at an exterior of the esophageal wall. In some instances, the temperature alteration zone 124 may be relatively small (although intense) near the position of the external heat source and may expand toward an opposing side of the esophageal wall. The length $L_A$ may also be referred to as a longitudinal length of the temperature alteration zone 124, as this length is measured in a direction corresponding to a longitudinal axis of the esophagus. The heat sensing region 122 can fully extend through the temperature alteration zone 124. For example, in the illustrated embodiment, and as discussed above, the heat sensor 120 is positioned such that a distal end thereof is distal to the temperature alteration zone 124 and such that a proximal end thereof is proximal to the temperature alteration zone 124.

Figure 2:
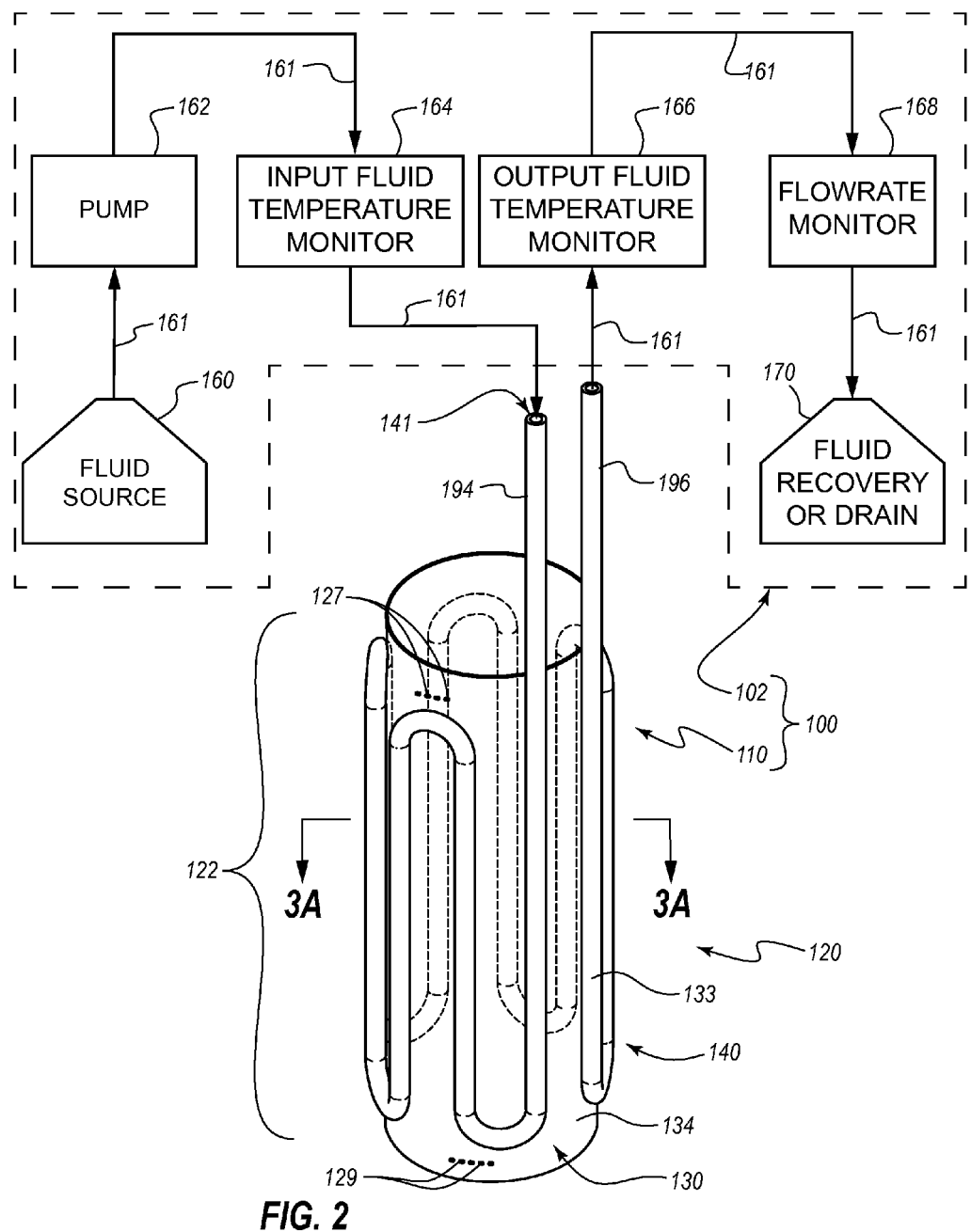
FIG. 2 is a schematic view of the heat sensing system of FIG. 1 and includes a perspective view of the heat sensor of FIG. 1.

FIG. 2 schematically depicts the heat sensing system 100, with a distal end of the heat sensing assembly 110, which includes the heat sensor 120, shown in perspective. The heat sensor 120 can be configured to contact an inner surface of the esophagus 60, as further discussed below. The heat sensor 120 comprises a support structure 130 that can aid in achieving this contact and, in some embodiments, can support or carry other components of the heat sensor 120 that make direct contact with the esophagus 60. In the illustrated embodiment, the support structure 130 includes a support layer or substrate 134, which defines a tube.

The heat sensor 120 can also include a heat sensing structure 140, which can be carried by the support structure 130. In the illustrated embodiment, the heat sensing structure 140 comprises a fluid conduit 133. In the illustrated embodiment, the fluid conduit 133 defines a serpentine pattern, which extends up and down along a longitudinal length of the heat sensor 120 and encompasses an entirety of a perimeter of the heat sensor 120. In other embodiments, the heat sensing structure 140 (e.g., the conduit 133) may encompass only a portion of the support structure 130, as discussed further below. In other or further embodiments, the conduit 133 may define a patterned, irregular, or non-repeating path about the substrate 134.

The conduit 133 can be formed of one or more materials that are flexible and/or capable of conducting heat. For example, the conduit 133 can be configured to permit heat transfer to, from, or both to and from fluid flowing through a fluid passageway, fluid path, or lumen 141 defined by the conduit 133. Accordingly, the heat sensing structure 140 may also be referred to as a heat transfer structure 140. In other or further embodiments, the conduit 133 can comprise a biocompatible material that can contact portions of a patient's anatomy without adverse effects. Similarly, the support structure 130 can comprise one or more flexible and/or biocompatible materials, as discussed further below. In some embodiments, the heat sensor 120 can be devoid of metallic material or other forms of material that might, in some instances, be capable of attracting or conducting electrical energy from the ablation tip 72 during an ablation procedure.

The conduit 133 can be attached to the substrate 134 in any suitable manner, such as, for example, via adhesives and/or welding (e.g., ultrasonic welding). In some embodiments, the substrate 134 and the conduit 133 can comprise a unitary piece of material. In the illustrated embodiment, the conduit 133 includes two fluid path extensions or fluid passageway branches 194, 196 that can permit fluid communication between the heat sensor 120 and more proximally positioned portions of the heat sensing assembly 110, such as the connector 112 (see FIG. 1). The branches 194, 196 may also be referred to as conduits. In some embodiments, the branches 194, 196 may be incorporated into the catheter 114 (e.g., may define lumens within the catheter 114), or they may be separate from the catheter 114. For example, in some embodiments, the branch 194, which may be an inlet branch, and the branch 196, which may be an outlet branch, significantly longer than what is depicted. For example, the inlet and outlet branches 194, 196 may extend through the esophagus of the patient and out of the nose or mouth of the patient, in some arrangements. In some embodiments where the branches 194, 196 are separate from the catheter 114, the branches 194, 196 may terminate within the esophagus and may be in fluid communication with individual lumens defined by the catheter 114.

The conduit 133 can extend continuously in both a longitudinal direction (e.g., the direction of the central axis of the illustrated sensor 120) and in one or more lateral directions that are transverse to the longitudinal direction (e.g., perpendicular to or any other direction that is non-collinear with or nonparallel to the longitudinal direction). For example, in the illustrated embodiment, the conduit 133 has portions that extend in the longitudinal direction, which is a substantially vertical direction in the orientation shown in FIG. 2. The conduit 133 further extends about the perimeter or circumference of the substrate 134 of the illustrated sensor 120. Those portions of the conduit 133 that extend peripherally or circumferentially may be said to extend in two transverse directions that are perpendicular to the longitudinal direction. For example, if the longitudinal direction is defined as the Z-axis of the sensor 120, and if a plane that is perpendicular to the Z-axis includes perpendicular X- and Y-axes, then it may be said that the conduit 133 extends in the Z-direction (longitudinally) and in both the X- and Y-directions (two lateral directions that are perpendicular to the longitudinal direction). Stated otherwise, the conduit 133 has various portions that include components in each of the X-, Y-, and Z-directions. The conduit 133 extends in multiple directions to define the heat sensing region 122. It may also be said that conduit 133 is fixed to the substrate 134 in a circuitous path. The heat sensing region 122 thus extends over a finite area that is significantly greater than a single point. For example, thermocouples generally sense temperatures at a single point, which is at a junction of wires that comprise different materials. In contrast, the heat sensing region 122 defined by the heat sensing structure 140 can span an area that is much greater than the limited region that can be sensed by such thermocouples. In the illustrated embodiment, the heat sensing region 122 extends along the distance $L_S$ in the longitudinal direction. The heat sensing region 122 can further extend about a majority of a perimeter of the support structure 130. In various embodiments, the heat sensing region 122 can extend around no less than about ⅓, ½, ⅔, or ¾ of a perimeter of the support structure 130. In some embodiments, the heat sensing region 122 can extend about an entirety of the perimeter.

The heat sensor 120 can be sensitive to temperature changes that occur anywhere within the heat sensing region 122. For example, in some arrangements, if only a small portion of the conduit 133 is heated, a temperature of heat transfer fluid that is flowing through that portion of the conduit will increase. In various embodiments, it can be determined that some amount of heating (or cooling) has occurred along at least a portion of the length of the conduit 133 when the heat transfer fluid exits from the heat sensor 120 with a temperature different from that at which it entered the heat sensor 120. In some embodiments, it may be sufficient to determine that a temperature change of a sufficient magnitude has been effected anywhere within the heat sensing region 122 in order to conclude that damage to the esophagus 60 or other bodily structures may occur if ablation continues. Any suitable determination based on readings or measurements from the heat sensor 120 may be made by the controller 102. In view of functionalities of various embodiments of the heat sensor 120, the term "heat sensor" is sufficiently broad to include sensors and processes that detect a change in temperature, whether that change is an increase or a decrease (e.g., heating, as an increase in heat, or cooling, as a decrease in heat), even if the sensor does not determine what the temperature is at a given point and/or does not provide information from which the temperature can be determined. For example, the term "heat sensor" can include a "temperature change sensor," which is a sensor that is capable of detecting a change in temperature (e.g., due to heating or cooling) anywhere within a sensing region of the sensor. The sensor may be capable of detecting such a temperature change, even where the change occurs at only a portion of the sensing region. Similarly, the term "heat sensing" is sufficiently broad to include "temperature change sensing," in which changes in temperature (e.g., heating or cooling) are detected, even if an exact or specific temperature is not determined.

In some embodiments, multiple conduits 133 may be used and arranged in any suitable pattern so as to determine the position at which temperature has changed. For example, in embodiments different from that which is depicted in FIG. 2, the heat sensor 120 includes two conduits that each define a serpentine pattern that doubles back on itself, as shown, but is confined to only one side (e.g., opposing 180-degree swaths) of a substantially cylindrically shaped substrate 134. It may be said that the separate conduits define an array, grid, pattern, mesh, or lattice, which provides for a sensitive heat sensing region 122. Other arrangements of the conduits are also possible. The array can be configured to provide information regarding a specific region of the heat sensing structure 140. For example, given the particular arrangement of the two-conduit arrangement just described, the temperature change of heat transfer fluid exiting one conduit can be compared with the temperature change of heat transfer fluid exiting the other conduit so as to determine the differences in heating (or cooling) at one side of the heat sensor 120 relative to the other side of the heat sensor 120. In other or further embodiments, multiple conduits may be positioned at different longitudinal positions, such that information may be obtained as to the longitudinal position of the sensor 120 at which heating takes place. In view of the foregoing, in some embodiments, multiple conduits are used in parallel to detect heat sources occurring in different regions of the temperature alteration zone 124 and/or at different positions within the heat sensing region 122.

However, in some embodiments, the actual position at which heating (or cooling) occurs within the esophagus 60 may not be important, so long as the heat sensor 120 is positioned to sense any temperature change due to an ablation procedure. That is, so long as any temperature change or heating due to the ablation procedure can be determined and monitored by any portion of the sensor 120, the temperature, or temperature change, information obtained by the heat sensor 120 may be sufficient. Such information can be used, for example, to conclude that the ablation procedure should be at least temporarily delayed or halted so as to prevent undesired damage to the esophagus 60 and/or other anatomical structures.

Accordingly, in various embodiments, the heat sensing structure 140 may comprise a single conduit. In still further embodiments, the heat sensing structure 140 may comprise two or more, three or more, or four or more conduits. The conduit or conduits may be arranged in any suitable configuration so as to define a relatively large heat sensing region 122. One or more conduits may also be arranged as desired in any number of longitudinal positions and/or radial positions to permit provide information regarding the specific region or regions of the sensor 120 at which temperature changes occur. In some embodiments, a conduit or conduits may also have large openings or spaces 171 between adjacent branches thereof, such that a width of each space 171 is many times (e.g., 5, 10, 50, or 100 or more times) greater than a diameter of the conduit. The large openings or spaces may permit the heat sensing structure 140 to be more compliant, as compared with more compactly spaced conduits. However, in other embodiments, the conduits may be more tightly compacted, but may be relatively flexible. In either case, the sensing structure 140 may be configured to yield to natural movements of the esophagus 60.

In certain embodiments, the heat sensor 120 includes one or more imaging markers 127, 129 for visualization of the heat sensor 120 during placement and/or use via fluoroscopy or any other suitable imaging technique. In the illustrated embodiment, an imaging marker 127 is placed at the proximal end of the heat sensor 120 and another imaging marker 129 is placed at the distal end of the heat sensor 120. Other arrangements and placements of the one or more imaging markers 127, 129 is also possible. Each marker 127, 129 may comprise any suitable substance, such as, for example, silver, gold, bismuth, cesium, thorium, tin, zirconium, tantalum, tungsten, and/or lanthanum and/or compounds thereof. In some embodiments, the markers 127, 129 may be referred to as radiopaque markers. The same or similar makers may be used with any of the heat sensors disclosed herein.

Figure 3B:
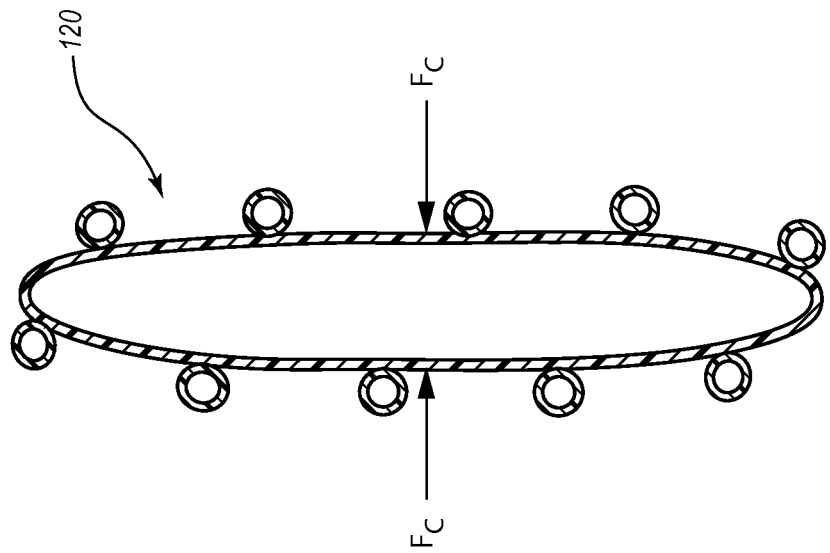
FIG. 3B is another cross-sectional view of the heat sensor of FIG. 1, similar to that shown in FIG. 3A, wherein the heat sensor is shown in a displaced or compressed state, which may also be referred to as a compliance state.
Figure 3A:
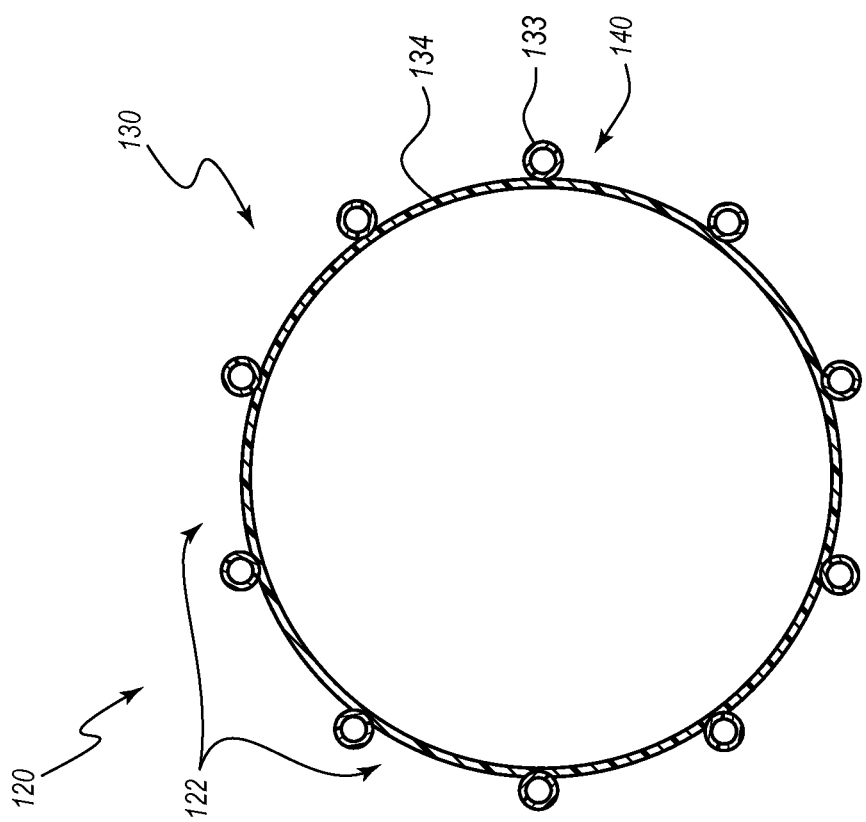
FIG. 3A is a cross-sectional view of the heat sensor of FIG. 1 taken along the view line 3A-3A in FIG. 2, wherein the heat sensor is shown in a natural or uncompressed state.

With reference to FIGS. 3A and 3B, the heat sensor 120 can be configured to transition between a natural or uncompressed state (FIG. 3A) and a displaced or compressed state (FIG. 3B), which may also be referred to as a compliance state. In the illustrated embodiment, the support structure 130 and/or the heat sensing structure 140 comprise one or more elastically resilient and flexible materials that are biased toward the orientation shown in FIG. 3A, and the heat sensor 120 can be displaced or deformed to other orientations, such as that shown in FIG. 3B, upon application of forces thereto (e.g., the compression forces $F_C$). Upon removal or discontinuance of the displacement or deforming forces, the heat sensor 120 can return to its uncompressed state. In certain embodiments, the biasing forces that arise within the support structure 130 and/or the heat sensing structure 140 when deformed are relatively small in comparison to the forces applied by the esophagus 60, such that the heat sensor 120 is very compliant with respect to the esophagus 60. Accordingly, in some embodiments, the bias is sufficient to maintain the heat sensor 120 in an expanded state so as to contact and/or be in close proximity to an inner wall of the esophagus 60 without deforming the esophagus 60, or without substantially deforming the esophagus 60. For example, the heat sensor 120 can be sufficiently compliant to permit the esophagus 60 to be in a substantially relaxed or collapsed state, and will not expand the esophagus 60 into closer proximity to the atrial wall 72 of the heart 70, yet the heat sensor 120 tracks, follows, conforms to, complies with, or accords with an inner surface of the esophagus 60. Such an arrangement is depicted in FIGS. 3B-5, as discussed further below, and may be referred to as a compliance state or as a tracking, following, conformance, or according state. As used herein, the term "without substantially deforming" includes situations in which no deformation takes place, but also includes situations in which negligible deformation takes place. For example, the support structure 130 may press against an inner surface of the esophagus 60 and may slightly compress the esophageal wall and/or may slightly displace or deform the esophageal wall. However, such deformations will not be significant, and may only move the esophageal wall marginally closer to the ablation site. In some instances, "substantial deformation" can be defined as increasing or decreasing one or more of the maximum transverse width (e.g., maximum diameter) and the minimum transverse width (e.g., minimum diameter) of the esophagus by an amount greater than 20 percent of the original magnitude thereof.

In the illustrated embodiment, the support structure 130 comprises a tube or sheath, which may be substantially cylindrical when in the uncompressed state, as shown in FIG. 3A. When positioned within the esophagus 60, the support structure 130 may be compressed into an oblong or ovoid configuration, such as that depicted in FIGS. 3B-5. If the esophagus 60 expands or becomes more cylindrical under normal or natural conditions, or upon other removal of the compressive forces $F_C$ (such as removal of the heat sensor 120 from the esophagus 60), the support structure 130 can move toward or return to the uncompressed configuration. The support structure 130 thus may be configured to maintain contact with, or otherwise maintain close proximity to, the inner surface of the esophagus 60. Similarly, in the illustrated embodiment, the heat sensing structure 140, or the conduit 133, is arranged in a circular pattern about the support structure 130. The conduit 133 may flex radially in manners such as just discussed with respect to the support structure 130. Maintaining contact or close proximity between the heat sensor 120 and the inner wall of the esophagus 60 can permit effective thermal transfer from the esophageal wall to the heat sensor 120. The esophagus 60 is depicted in a flattened cylindrical state, but any natural state of the esophagus is contemplated, including, for example, highly convex and/or convolute orientations.

As previously discussed, the support structure 130 and/or the heat sensing structure 140 may be flexible, malleable, or readily conformable so as to be displaced, compressed, transformed, altered, or reshaped into an orientation that tracks, follows, conforms to, complies with, or accords with an inner surface of the esophagus 60. Moreover, in the illustrated embodiment, the support structure 130 is resiliently flexible and is biased toward a natural configuration (e.g., a cylinder) that provides a degree of structural rigidity to the support structure 130. However, in other embodiments, the support structure 130 may not be biased toward a natural shape, and may instead be even more compliant, or stated otherwise, may be flaccid, limp, or slack. The heat sensing structure 140 may have the same properties as the support structure 130. For example, in some embodiments, heat sensing structure 140 may be flexible, but may not have as much structural integrity or rigidity as the support structure 130. Certain embodiments may be pressed toward or against the interior wall of the esophagus 60 via additional structural features, such as a balloon, and may even be maintained against the interior wall via these structural features. In other or further embodiments, contact may be maintained between the support structure 130 and/or the heat sensing structure 140 and the esophagus 60 via one or more of surface tension (e.g., due to moisture on the esophagus wall), adhesives, and/or other suitable fixing elements. Certain of such alternative embodiments are discussed further below. As previously mentioned, the heat sensing structure 140 may also exhibit heat conducting properties. In various embodiments, a support structure 130 and/or a heat sensing structure 140 having any of the foregoing properties can comprise one or more biocompatible materials, such as biocompatible plastics, such as, for example, one or more of polyethylene (PE), polypropylene (PP), nylon, or polyvinyl chloride (PVC). A thickness of the support structure 130 can be within a range of from about 0.001 inches to about 0.040 inches, or may be no greater than about 0.001, 0.002, 0.003, 0.004, 0.005, 0.010, 0.020, 0.030, or 0.040 inches. A thickness of the walls of the conduit 133 can be within a range of from about 0.001 inches to about 0.040 inches, or may be no greater than about 0.001, 0.002, 0.003, 0.004, 0.005, 0.010, 0.020, 0.030, or 0.040 inches.

The support structure 130 and or the heat sensing structure 140 can be flexible, resiliently flexible, and/or compliant, e.g., in manners just described. Accordingly, the heat sensor 120 can be flexible, resiliently flexible, and/or compliant. Flexibility of the heat sensor 120 may be about a single axis, in some embodiments, or the flexibility may be about multiple axes in other embodiments. For example, in some embodiments, the heat sensor 120 may extend longitudinally and may be flexible about any axis that is perpendicular to a longitudinal axis of the heat sensor 120. In this manner, the illustrated embodiment can be bent in any direction and may conform to longitudinal curves of the esophagus. In other or further embodiments, the heat sensor 120 can be flexible about the longitudinal axis itself and/or about any axis parallel thereto. For example, in the illustrated embodiment, the heat sensor 120 is also flexible in this manner, such that an outer surface of the heat sensor 120 is capable of conforming to an inner periphery of the esophagus 60. Stated otherwise, the heat sensor 120 can be flexible along its longitudinal length and/or in directions that are transverse to the longitudinal length. Accordingly, in various embodiments, the heat sensor 120 can be configured to conform to curves or bends along a length of the esophagus and/or to an inner periphery of the esophagus at any lateral cross-section of the esophagus.

With continued reference to FIGS. 3A and 3B, in various embodiments, the heat sensing region 122 can extend about a significant portion of a lateral cross-section of the heat sensor 120. In the illustrated embodiment, the conduit 133 is at an exterior of the flexible support structure 130. In other embodiments, the conduit 133 can be at an interior of the support structure 130. In still other or further embodiments, one or more conduits 133 can be at an interior and an exterior of the support structure 130 and/or can extend through a wall of the support structure 130. The cross-sectional view of the heat sensor 120 shown in FIGS. 3A and 3B may generally be referred to as a "perimeter" of the heat sensor 120. In the illustrated embodiment, the perimeter is substantially circular in FIG. 3A and is substantially ovoid in FIG. 3B. In various embodiments, a diameter of the heat sensor 120 can be within a range of from about 0.375 inches to about 1.25 inches, or no less than about 0.4, 0.5, 0.75, 1.0, or 1.25 inches.

As can be seen in FIGS. 3A and 3B, the conduit 133 extends about the full perimeter of the substrate 134. In various embodiments, one or more conduits 133 extend along, or about, no less than $1/4$, $1/3$, $1/2$, $2/3$, or $3/4$ of a perimeter of the substrate 134. Stated otherwise, the heat sensing region 122 can extend circumferentially about no less than $1/4$, $1/3$, $1/2$, $2/3$, or $3/4$ of a perimeter of the substrate 134. As the substrate 134 may generally conform to an interior surface of the esophagus (or to a formation that is substantially parallel to the interior surface), the heat sensing region 122 likewise may extend circumferentially about no less than $1/4$, $1/3$, $1/2$, $2/3$, or $3/4$ of, or about no less than a majority of, an inner perimeter of the esophagus 60.

With reference again to FIG. 2, portions of the heat sensing system 100 are shown in greater detail, although they are depicted schematically. In particular, the heat sensing system 100 can include a fluid source 160, which provides a supply of transfer fluid 161, a pump 162, an input fluid temperature monitor 164, and an output fluid temperature monitor 166. In some embodiments, the heat sensing system 100 further includes a flowrate monitor 168 and/or a fluid recovery receptacle 170. In various embodiments, the controller 102 can be in electrical communication with one or more of the pump 162, the temperature monitors 164, 166, and the flowrate monitor 168. As previously mentioned, the controller 102 may be capable of carrying out methods and processes discussed hereafter. For example, the controller 102 may include hardware and/or software that is programmed, or programmable, to control one or more of the components of the heat sensing system 100 to carry out various processes. Communicative connections between the controller 102 and the various components of the heat sensing system 100 are not shown in FIG. 2. In some embodiments, one or more of the elements depicted schematically in FIG. 2 may be incorporated into the controller 102 (e.g., may share a common housing with the controller 102). This is shown by a broken line in FIG. 2, which depicts that the components are incorporated into the controller 102. In other embodiments, the components are physically separate from the controller 102, but may be fluidly and/or communicatively connected to the controller 102 (e.g., via fluid conduits and/or electrical leads).

The pump 162 can move heat transfer fluid 161 through the heat sensing system 100. In particular, in the illustrated embodiment, the pump 162 moves heat transfer fluid 161 from the fluid source 160 to the input fluid temperature monitor 164, through the heat sensor 120, to the output fluid temperature monitor 166, to the flowrate monitor 168 and to the fluid recovery receptacle 170. Any suitable fluid connections between the various components of the heat sensing system 100 are possible, and are schematically represented by arrows that show the direction of fluid flow.

The heat transfer fluid 161 can comprise any suitable fluid. It may be desirable for the heat transfer fluid 161 to be non-toxic or otherwise suitable for ingestion by a patient in the event of a leak. However, in some embodiments, it may be most desirable for the heat transfer fluid 161 to have particular heating characteristics, such as a desired specific heat, and precautions may be made where such fluids may potentially harmful if ingested. In some embodiments, the recovered heat transfer fluid 161 is cycled from the fluid recovery receptacle 170 to the fluid source 160. For example, in some embodiments, these components may comprise a common fluid reservoir.

In other embodiments, rather than having a fluid recovery receptacle 170, the heat transfer fluid 161 may instead be drained after it exits the output fluid temperature monitor 166. In certain of such embodiments, the flowrate monitor 168 may be placed at a more upstream portion of the circuit (e.g., at the pump 162, before or after the input fluid temperature monitor 164, or before the output fluid temperature monitor 166). In some embodiments, the drainage may take place at an exterior of the patient. For example, the fluid temperature monitor 166 and the flowrate monitor 168 may be at an exterior of a patient and the heat transfer fluid 161 can be expelled therefrom. In other embodiments, the fluid temperature monitor 166 may be relatively small and may be positioned at or near the end of the output conduit 196, which may be at an interior of the esophagus. In certain of such embodiments, used heat transfer fluid 161 may drain into the esophagus 60 and may proceed to the patient's stomach. In certain of such embodiments, the heat transfer fluid 161 may comprise water, air, saline solution, or some other ingestible fluid.

The input and output fluid temperature monitors 164, 166 can comprise any suitable temperature sensors. For example, in some embodiments, the temperature monitors 164, 166 each include thermocouples. The flowrate monitor 168 may be of any suitable variety. Moreover, the flowrate monitor 168 and/or the pump 162 may be situated at other positions within the circuit. For example, the pump 162 may be positioned after the output fluid temperature monitor 166 and/or the flowrate monitor 168 may be positioned before the input fluid temperature monitor 164. In other embodiments, the pump 162 and flowrate monitor 168 may be adjacent to one another and/or may be incorporated into a single device. In other embodiments, such as in the system discussed below with respect to FIG. 15, one or more of the pump and flowrate monitor 168 can be omitted.

Figure 4:
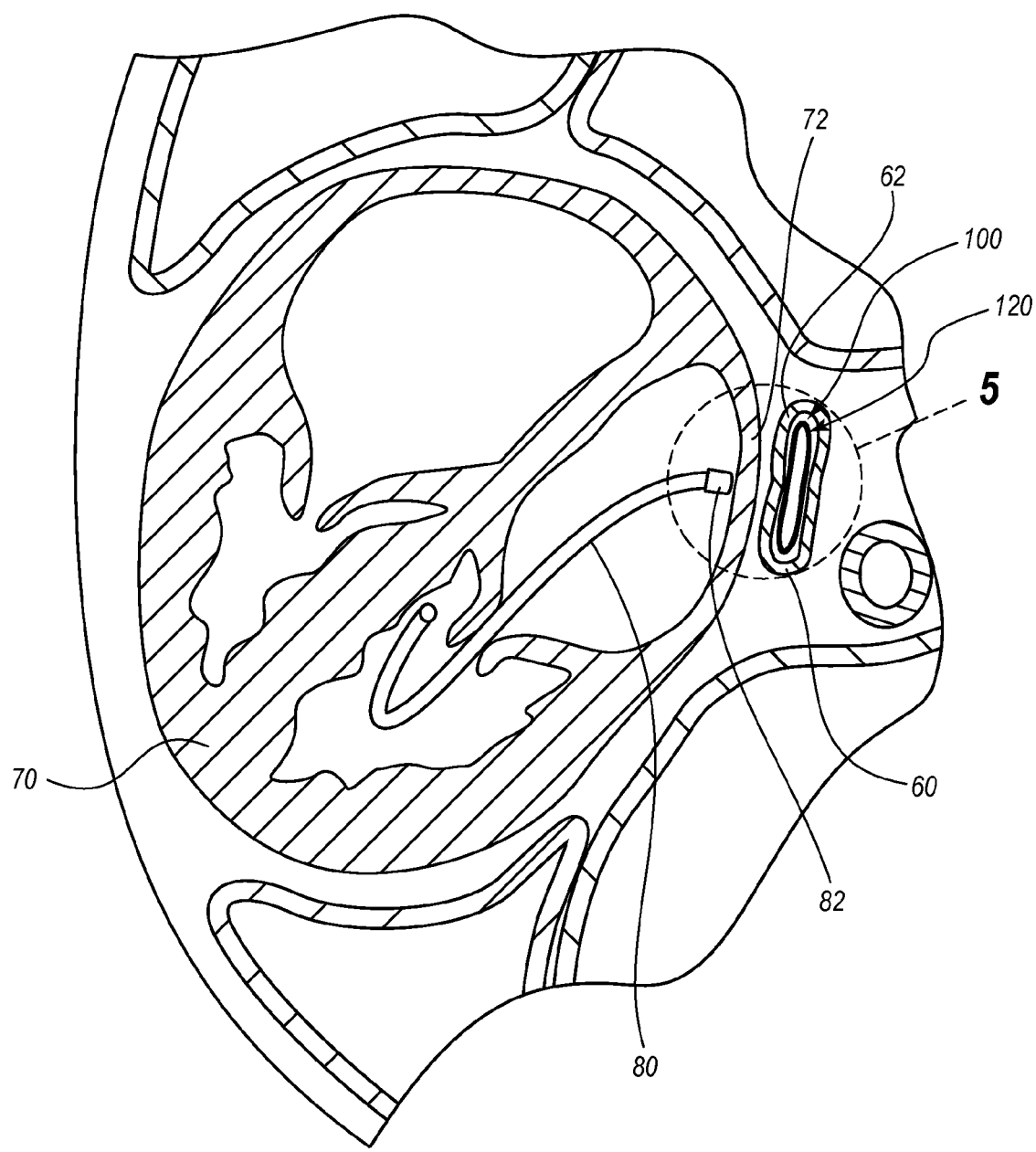
FIG. 4 is a cross-sectional view of the heat sensor of FIG. 1 positioned within the patient, taken along the view line 4-4 in FIG. 1.
Figure 5:
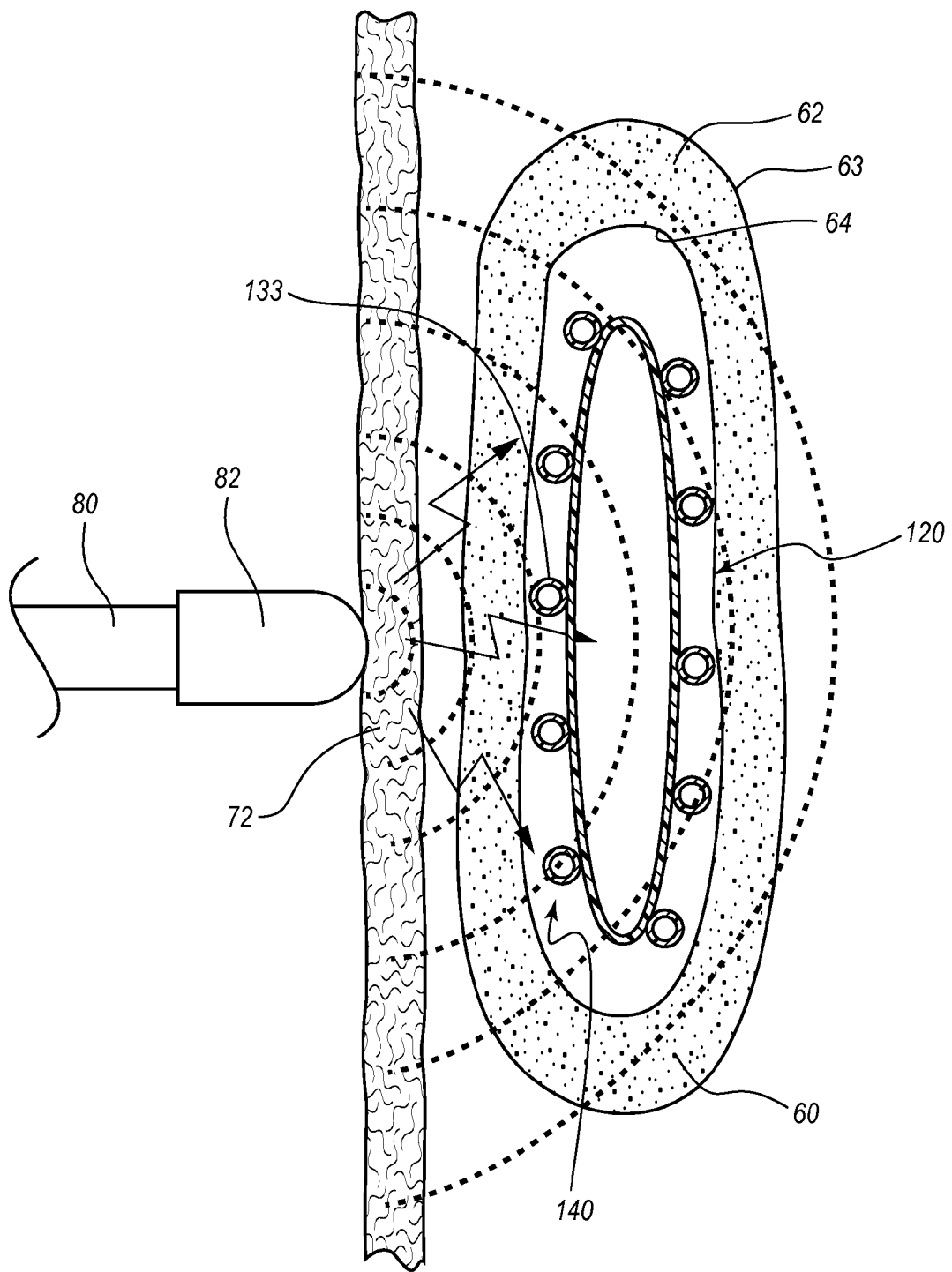
FIG. 5 is an enlarged view of FIG. 4, taken along the view line 5 therein, which includes a schematic depiction of heating of the atrial wall, the esophagus, and the heat sensor.

FIGS. 4 and 5 illustrate use of the heat sensor 120, and more generally, the heat sensing system 100, during an ablation procedure. In the illustrated embodiment, an ablation tool 70 delivers energy to the atrial wall 72 via an ablative tip 72. The energy causes heating of the atrial wall 72, as desired, but also can cause heating of the wall 62 of the esophagus 60. The heating may be more intense at an outer surface 63 of the esophagus wall 62, as compared with an inner surface 64 thereof, as the esophageal tissue can be insulating. In the illustrated arrangement, the conduit 133 is placed in contact with the inner surface 64 of the esophagus 60. Cooling of the atrial wall 72 may proceed in a similar manner in cryoablation procedures.

Figure 6:
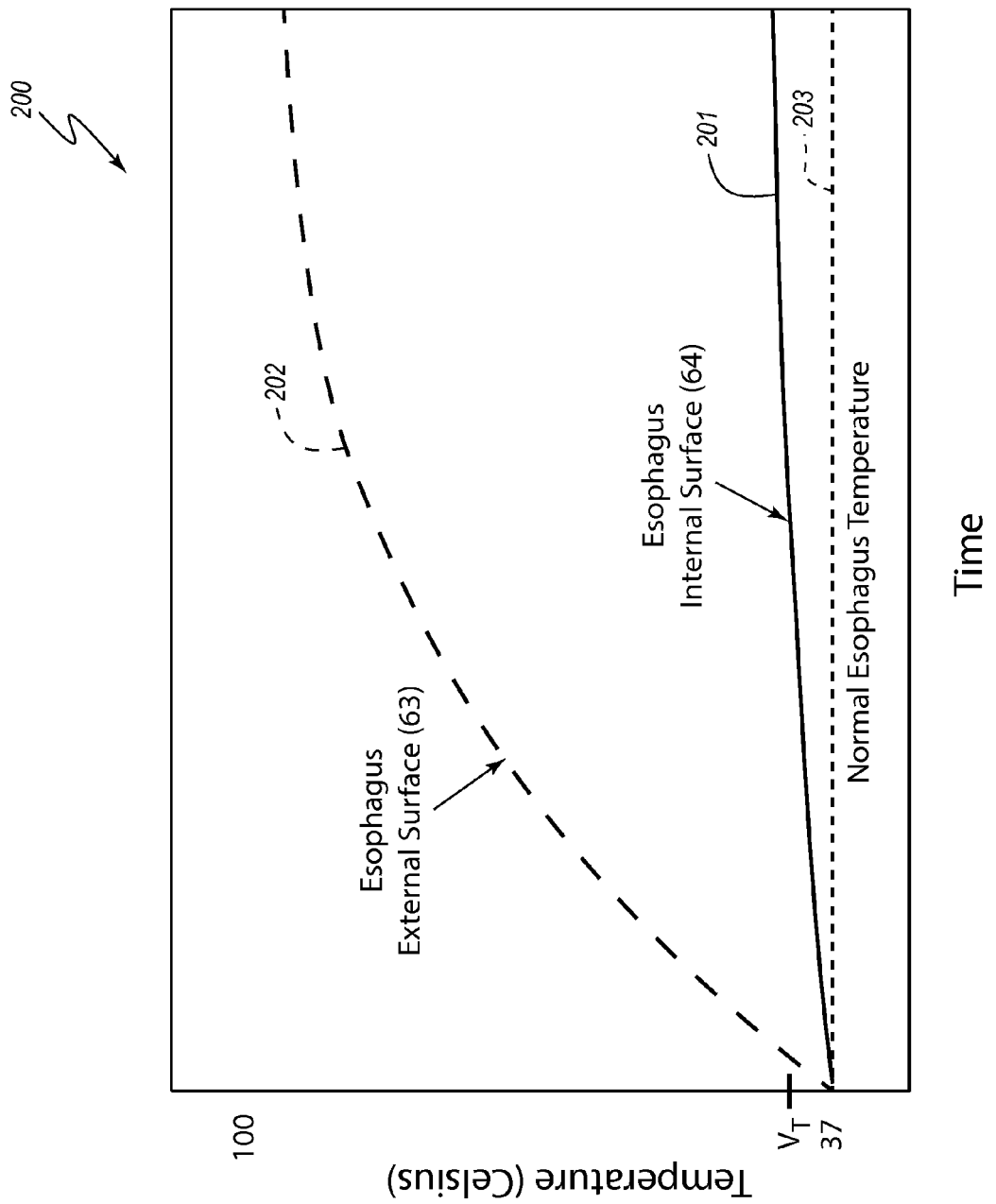
FIG. 6 is a plot that depicts illustrative heating patterns of different portions of the esophagus.

FIG. 6 depicts a plot 200 of a temperature profile 201 detected by the heat sensor 120 during an ablation procedure. More particularly, the plot depicts the temperature profile of the inner surface 64 of the esophagus 60, as detected by the heat sensing structure 140 of the heat sensor 120, during the ablation procedure. In addition to the temperature profile 201, the plot 200 also includes, for reference purposes, a temperature profile 202 of the external wall 63 of the esophagus 60, as well as a baseline profile 203 that depicts the normal esophagus temperature. Comparison of the profiles 201, 202 illustrates how the esophagus can insulate the heat sensor 120 such that temperature changes are less pronounced at the position of the heat sensor 120. Accordingly, it can be desirable for the heat sensor 120 to be sensitive to small temperature changes.

In certain embodiments, the heat sensing system 100 triggers an alarm when the temperature profile 201 reaches or exceeds a threshold value $V_T$. The alarm can signify to the surgeon that damage to the esophagus and/or other bodily structures may result if ablation continues. The alarm may be provided in any suitable manner, such as via an audible sound and/or a visible warning on the display 104 (see FIG. 1). In other or further embodiments, ablation may automatically be discontinued when the threshold value $V_T$ is reached. For example, the controller 102 can direct that power no longer be supplied to the ablation tool 70 when the threshold value $V_T$ is reached. In still other or further embodiments, the alarm may be triggered and/or ablation automatically discontinued when the rate of change of the temperature profile 201 reaches or exceeds a threshold rate. The actual value of the threshold value $V_T$ may be different than what is schematically represented in FIG. 6.

Figure 7:
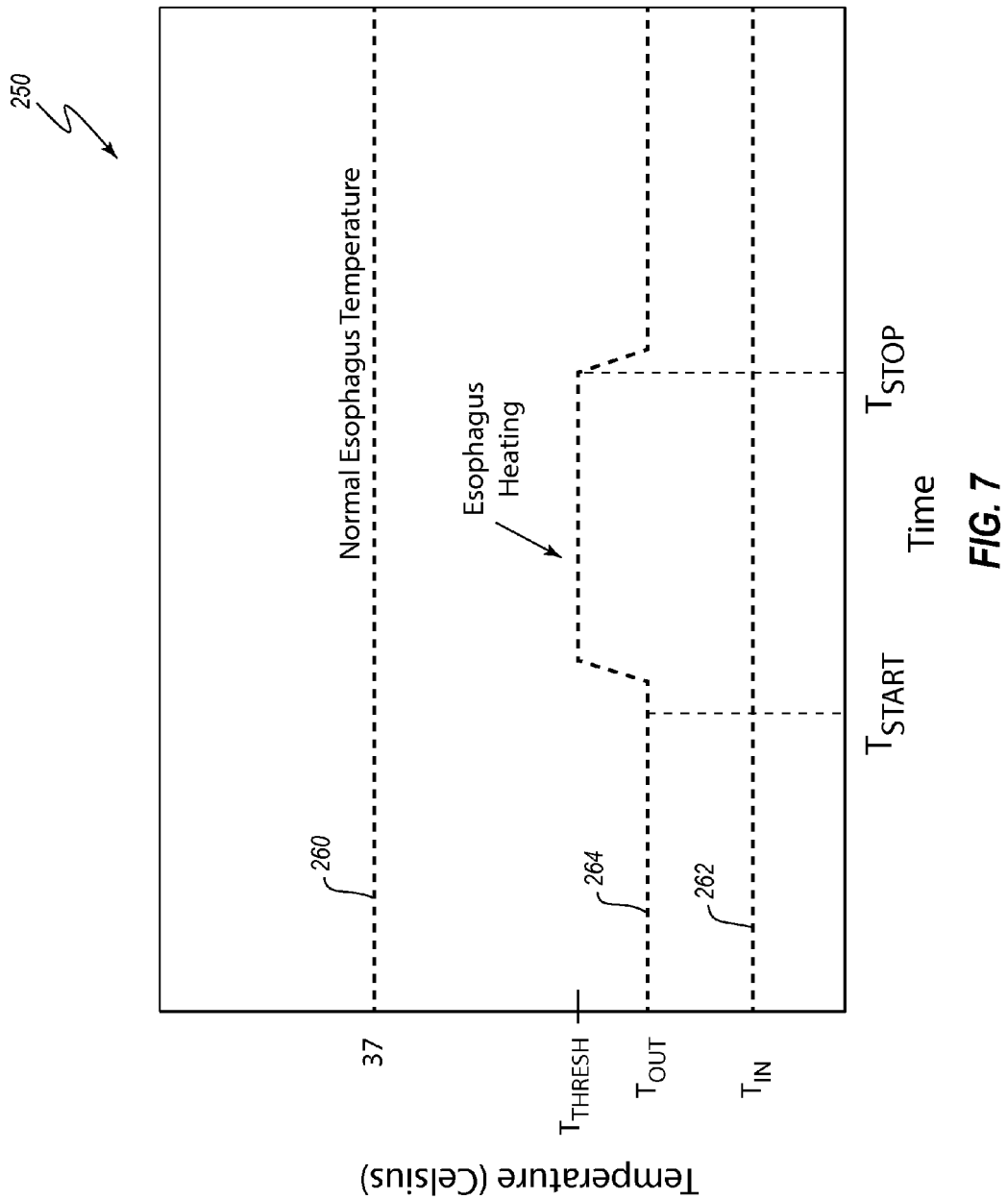
FIG. 7 is a plot that depicts an illustrative operational mode of the heat sensing system of FIG. 1.

FIG. 7 is an illustrative plot 250 of measurements that may be made by the input fluid temperature monitor 164 and the output fluid temperature monitor 166 of the heat sensing system 100 when the system is operating in an illustrative operational mode. In particular, the heat sensing system 100 is shown operating in a heat sensing mode in which the flowrate of the heat transfer fluid 161 is maintained substantially constant. In the illustrated embodiment, the heat transfer fluid 161 is introduced into the input branch 194 at a temperature $T_{IN}$ that is significantly lower than the normal temperature within the esophagus (e.g., body temperature, at 37 degrees Celsius). The input temperature $T_{IN}$ of the heat transfer fluid 161, as measured by the input fluid temperature monitor 164, is depicted by the curve 262, whereas the normal esophagus temperature is depicted by the curve 260. As the heat transfer fluid 161 flows through the conduit 133 at the interior of the esophagus, the heat transfer fluid 161 extracts a baseline amount of heat, such that the output temperature $T_{OUT}$ of the heat transfer fluid 161, as measured by the output fluid temperature monitor 166, is higher than the input temperature $T_{IN}$ by a relatively constant amount prior to ablation. Stated otherwise, the conduit 133 permits heat to pass through the wall thereof into the fluid passageway 141, and the heat thus admitted to the fluid passageway 141 is carried away via the heat transfer fluid 161 (e.g., heat sensor 120 carries heat away from the wall of the esophagus).

During an ablation procedure in which the esophageal wall is heated, the heat transfer fluid 161 can extract greater amounts of heat as it progresses through the heat sensor 120. The flow rate of the heat transfer fluid 161, which is measured by the flowrate monitor 168, can be used to determine the amount of energy that has been imparted to the heat transfer fluid 161. Additionally, depending on the flow rate of the heat transfer fluid 161 and the distance of the fluid path extending between the heating zone and the output fluid temperature monitor 166, detection of this increased amount of heating at the output fluid temperature monitor 166 can be slightly delayed. This slight delay is depicted by a small period between the time at which heating of the esophageal wall commences, $T_{START}$, and the time at which increasingly higher temperatures are observed by the output fluid temperature monitor 166, as reflected by the curve 264. A similar delay is present between the time at which ablation is stopped, $T_{STOP}$, and the time at which temperatures at the output fluid temperature monitor 166 drop to pre-ablation levels, as reflected by the curve 264. In some arrangements, this delay may be negligible.

In some embodiments, a threshold temperature $T_{THRESH}$ may be predetermined. The threshold temperature $T_{THRESH}$ may be the temperature at which an alarm or warning is provided alerting a practitioner that heating of the esophagus has reached undesirable levels and/or at which ablation is automatically stopped. In some arrangements, the alarm, warning, and/or automatic discontinuation of ablation takes place immediately upon detection of the threshold temperature $T_{THRESH}$ by the output fluid temperature monitor 166. In the illustrated embodiment, a delay is shown between the time at which the threshold temperature $T_{THRESH}$ is reached and the ablation procedure is terminated at $T_{STOP}$. In other or further embodiments, a temperature differential threshold, rather than (or in addition to) a set threshold temperature may be used in a similar manner. The temperature differential threshold can be the maximum allowable difference in temperature between the output temperature $T_{OUT}$ and the input temperature $T_{IN}$.

In some embodiments, the input temperature $T_{IN}$ may have a known value, and the input fluid temperature monitor 164 may be omitted. The output fluid temperature monitor 166 can be used to determine the temperature $T_{OUT}$ after the heat transfer fluid 161 has passed through at least a portion of the conduit 133 (e.g., the temperature monitor 166 may be placed at any suitable position along the length of the fluid passageway 141). In certain of such embodiments, the controller 102 may be configured to measure a change in a temperature of the heat transfer fluid after the heat transfer fluid has been conducted through at least a portion of the fluid passageway 141. This may be achieve by comparing the temperature detected by the monitor 166 and the known input temperature.

In some embodiments, it may be desirable to measure or monitor the normal esophagus temperature during the ablation procedure. This may be accomplished in any suitable manner, such as by use of a thermocouple distanced from an ablation site but in proximity to the heat sensing region 122. In some arrangements, this measurement may be used to dynamically vary threshold temperature $T_{THRESH}$ up or down, depending on whether the normal esophagus temperature rises or falls, respectively, independent of any ablation heating. In other arrangements, the normal esophagus temperature may not be measured, or any measurements thereof may not be used. Stated otherwise, in some embodiments, determination of whether to notify a practitioner and/or automatically terminate an ablation procedure may be based on changes in temperature relative to a baseline reading. For example, the value of $T_{THRESH}$ may be altered during the course of a procedure, and may, for example, be a set value relative to the normal esophagus temperature (e.g., $T_{THRESH}$=[Normal Esophagus Temperature−15 degrees Celsius]). In other embodiments, the determination of whether to notify a practitioner and/or automatically terminate an ablation procedure may be based on a fixed value of $T_{THRESH}$ that is independent of the actual temperature of the esophagus.

The example provided in FIG. 7 shows the heating curve for an ablation procedure in which the esophageal wall is heated. Because the input temperature $T_{IN}$ is lower than the normal esophagus temperature, the heat sensor 120 can cool the esophageal wall. The amount of cooling can be adjusted, as desired, such as by lowering the input temperature $T_{IN}$. Accordingly, the heat sensor 120 may act as a cooling device that can reduce or, in some instances, prevent harm to the esophageal wall during an ablation procedure. Stated otherwise, the heat sensor 120 can be configured to not only monitor heating of the esophageal wall during the ablation procedure, but can also cool the esophageal wall so as to reduce damaging of the wall due to the heating. In other arrangements, the heat sensor 120 may be used in cryoablation procedures. In certain of such arrangements, illustrative plots of the heat sensing system in operation 100 may be similar to the plot 250, with the exception that the curves 262 and 264 may be flipped, or mirrored, relative to the normal esophagus temperature curve 260.

As just discussed, certain embodiments of heat sensors disclosed herein can be used to cool the esophagus during an ablation procedure (or heat the esophagus, such as during cryoablation). For example, the heat sensor 120 discussed above can absorb heat from the esophagus. The temperature $T_{IN}$ of the heat transfer fluid 161 can be sufficiently low to cool the esophagus without damaging the esophagus. Accordingly, in some embodiments, the system 100 can be used to simultaneously monitor heating of the esophagus and cool the esophagus. The amount of cooling provided by the heat sensor 120 may be dependent upon such factors as the surface area of the tube 133, the temperature of the heat transfer fluid 161, and/or the flowrate of the fluid, and these or other properties may be preselected or adjusted to achieve a desired cooling (or heating) effect.

Other operational modes of the heat sensing system 100 are also possible. For example, in some embodiments, the temperature of the input fluid 161 may be altered (e.g., lowered) and/or the flowrate may be adjusted as an ablation procedure progresses.

Figure 8A:
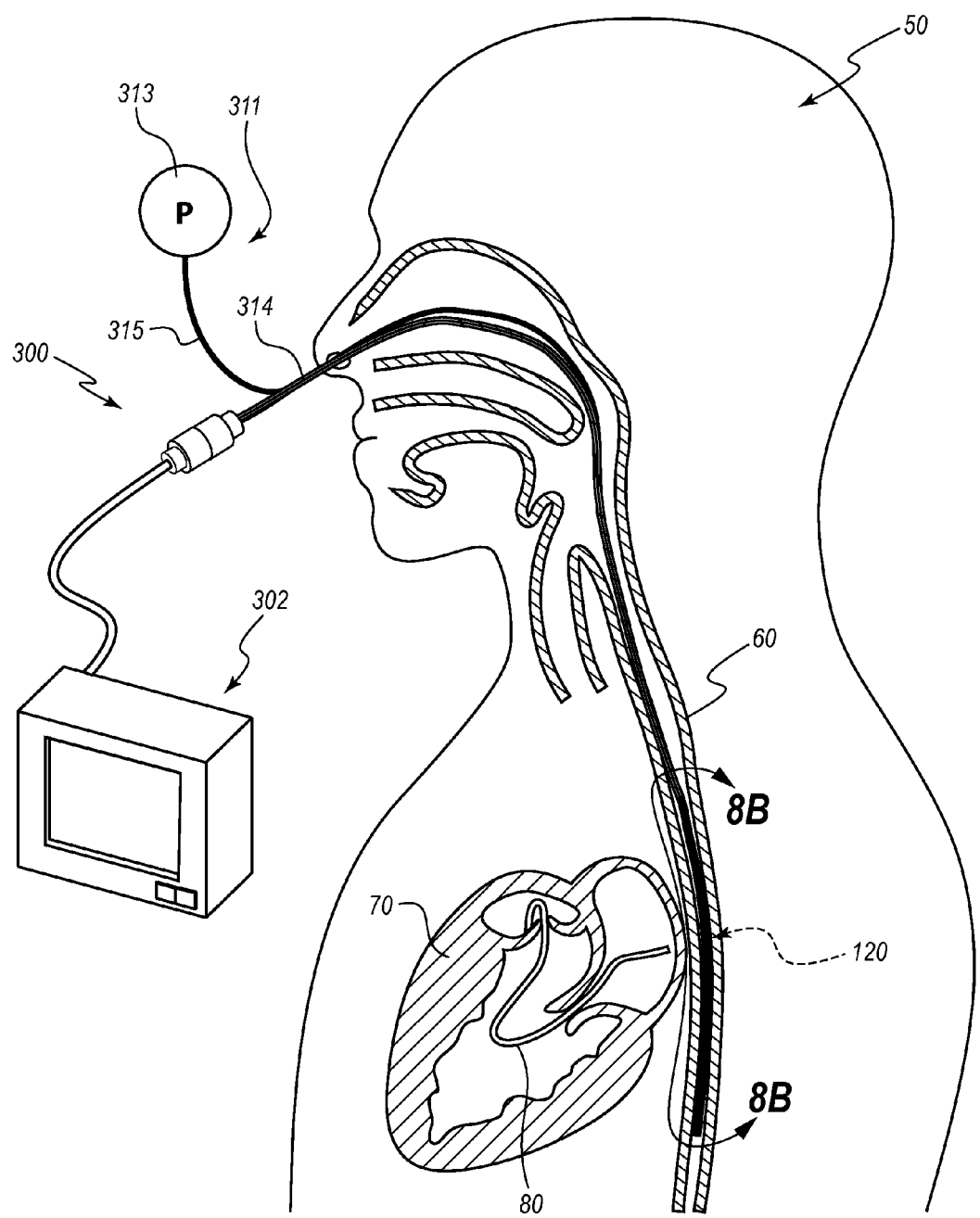
FIG. 8A is a perspective view of another embodiment of a heat sensing system that includes an inflation system for placement or deployment of the heat sensor within the patient, wherein an elevation view of the heat sensor is depicted in a packaged or undeployed state within the esophagus of the patient.

FIG. 8A illustrates another embodiment of a heat sensing system 300 that can resemble the heat sensing system 100 described above in certain respects. Accordingly, like features are designated with like reference numerals, with the leading digits incremented to "3." Relevant disclosure set forth above regarding similarly identified features thus may not be repeated hereafter. Moreover, specific features of the system 300 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 300. Any suitable combination of the features and variations of the same described with respect to the system 100 can be employed with the system 300, and vice versa. This pattern of disclosure applies equally to further embodiments depicted in subsequent figures and described hereafter, wherein the leading digits may be further incremented.

Like the heat sensing system 100, the heat sensing system 300 can include the heat sensor 120 discussed above or any other suitable heat sensor described herein. The heat sensing system 300 can further include an inflation system 311 configured to deploy the temperature sensor 120 within the esophagus 60 of the patient 50. In some embodiments, the heat sensing system 300 includes a monitor 302, such as the monitor 102 discussed above, which may include additional functionalities, such as the ability to sense, monitor, control, and/or display the pressure of an inflation fluid.

The inflation system 311 can include any suitable inflation device 313, such as, for example, those that are commonly used to deploy stents or the like. In some embodiments, the inflation device 313 can include a syringe that delivers inflation fluid to a fluid path 315 and can pressurize the fluid within the fluid path 315. It is noted that the term "fluid" may refer to one or more liquids and/or gases. The fluid path 315 can be incorporated into a catheter 314, such as the catheter 114 discussed above. For example, in some embodiments, the fluid path 315 includes one or more lumens that pass through at least a portion of the catheter 114. In other embodiments, the fluid path 315 may be separate from the catheter 114. For example, in some embodiments, a conduit that is separate from the catheter 114 may define the fluid path 315. The separate conduit may be movable relative to the catheter 114, and may be placed within the esophagus 60 separately from the catheter 114 and/or separately extracted from the esophagus 60.

In some embodiments, the inflation device 313 is configured to be controlled by the controller 302. For example, in some embodiments, a pressure sensor (e.g., a pressure transducer) can be couple to the fluid path 315 and can be in electrical communication with the controller 302. Based on pressure readings from the pressure sensor, the controller 302 can adjust the inflation device 313 to increase or decrease the pressure within the fluid path 315.

Figure 8C:
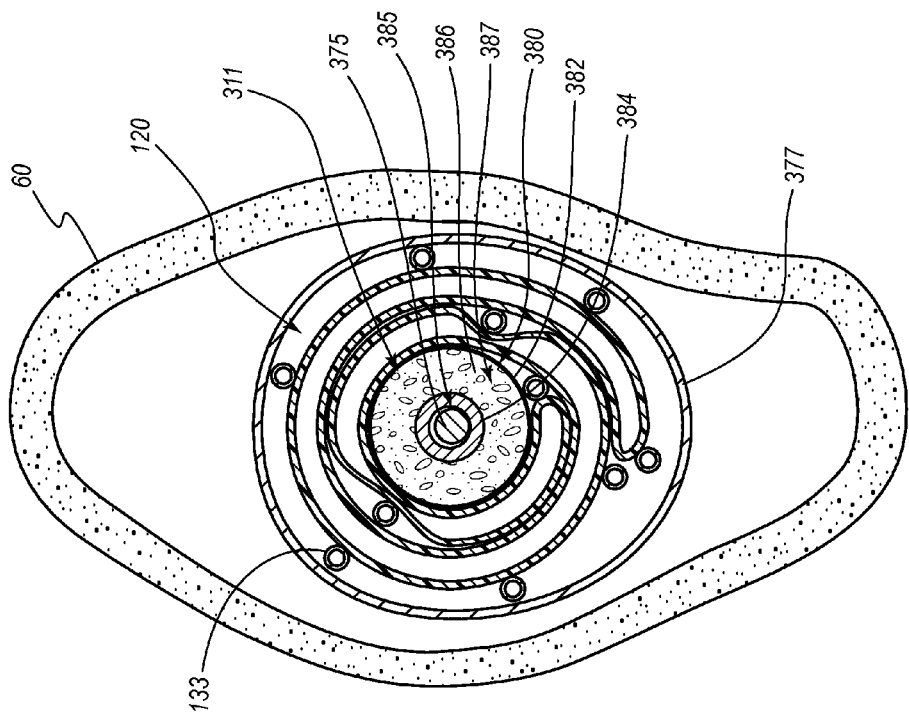
FIG. 8C is a cross-sectional view of the heat sensor and the portion of the inflation system within the esophagus of the patient taken along the view line 8C-8C in FIG. 8B.
Figure 8B:
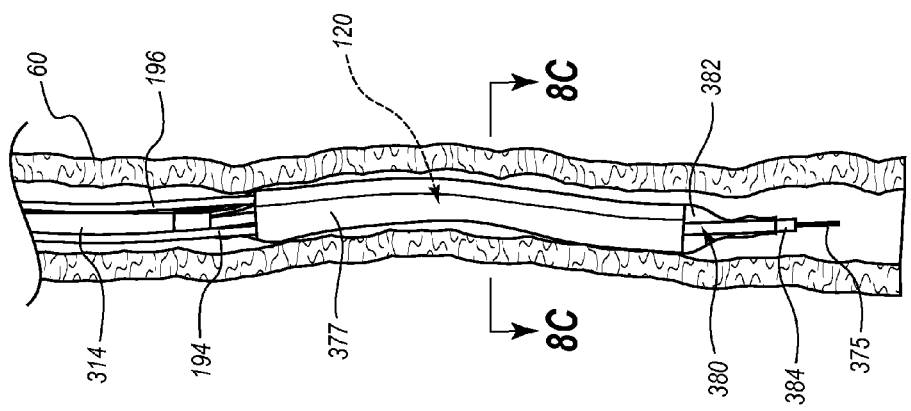
FIG. 8B is an enlarged view of the heat sensor and a portion of the inflation system within the esophagus of the patient taken along the view line 8B-8B in FIG. 8A.

FIGS. 8B and 8C illustrate the heat sensor 120 in a packaged, undeployed, folded, rolled, or compressed state, which facilitates insertion of the heat sensor 120 into the esophagus 60. In the illustrated embodiment, the heat sensor 120 includes a support structure 130 that has a substantially cylindrical natural configuration; however, the support structure 130 is folded and rolled into a low-profile configuration and is maintained in this configuration via a removable packaging sheath 377.

The inflation system 311 includes an inflation assembly 380 that is positioned at an interior of the heat sensor 120. The inflation assembly 380 includes an expandable balloon 382 and a wire sheath 384. The wire sheath 384 defines a lumen 385 that is sized to pass over a guide wire 375. A cavity 387 is provided between the balloon 382 and the wire sheath 384, which can be filled and pressurized with an inflation fluid 386. At the stage depicted in FIGS. 8A-8C, only a small amount of inflation fluid 386 is present within the balloon 380. In other embodiments, no inflation fluid 386 may be present within the balloon 380 at the illustrated stage.

Placement of the heat sensor 120 into the position shown in FIGS. 8A-8C can proceed as follows. The guide wire 375 is inserted into the esophagus 60 and advanced to a desired position, which may be substantially below the position at which the esophagus 60 is closest to the heart 70. The packaged heat sensor 120 and inflation assembly 380 are then advanced over the guide wire 375, with the wire sheath 384 sliding or otherwise passing over the guide wire 375. The packaging sheath 377 may then be removed. In the illustrated embodiment, the inlet and outlet branches 194, 196 of the conduit 133 are separate from, or are not incorporated into, the catheter 314 and are visible at an exterior of the catheter 314 in FIG. 8B.

Figure 9A:
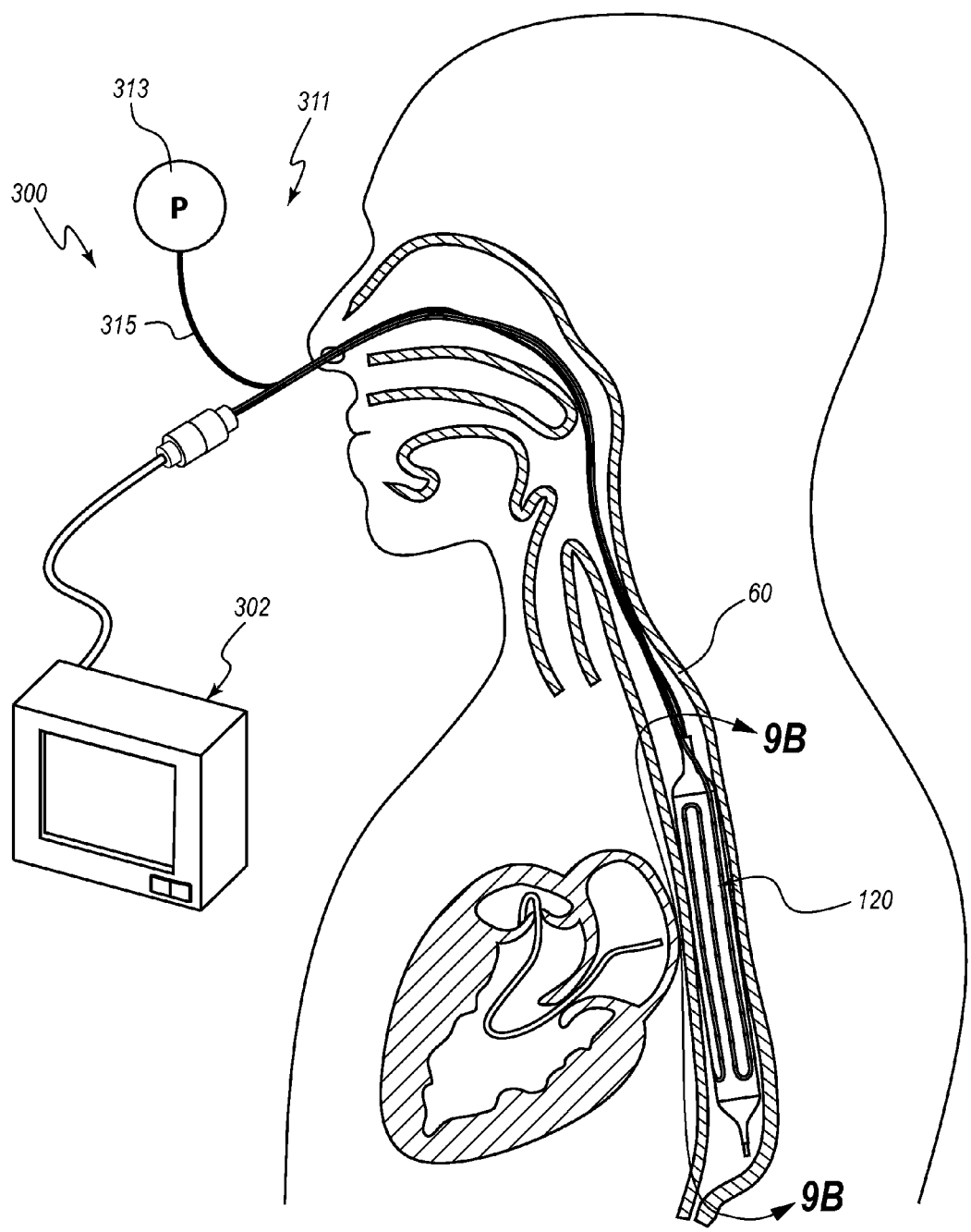
FIG. 9A is another elevation view of the heat sensing system of FIG. 1 being used in conjunction with the inflation system of FIG. 8A, wherein the heat sensor is depicted in an unpackaged or deployed state.

FIGS. 9A-9C illustrate a subsequent stage of placement of the heat sensor 120 within the esophagus 60. At this stage, the inflation device 313 is used to introduce additional inflation fluid 386 into the balloon 382, thereby causing the balloon 382 to expand. The balloon 382 may be expanded sufficiently far, or by a sufficient amount, to bring the conduit 133 into contact with and/or otherwise into close proximity to the inner surface 64 of the esophagus 60. The heat sensor 120 may be said to be in a deployed or expanded state in FIGS. 9A-9C.

Figure 10B:
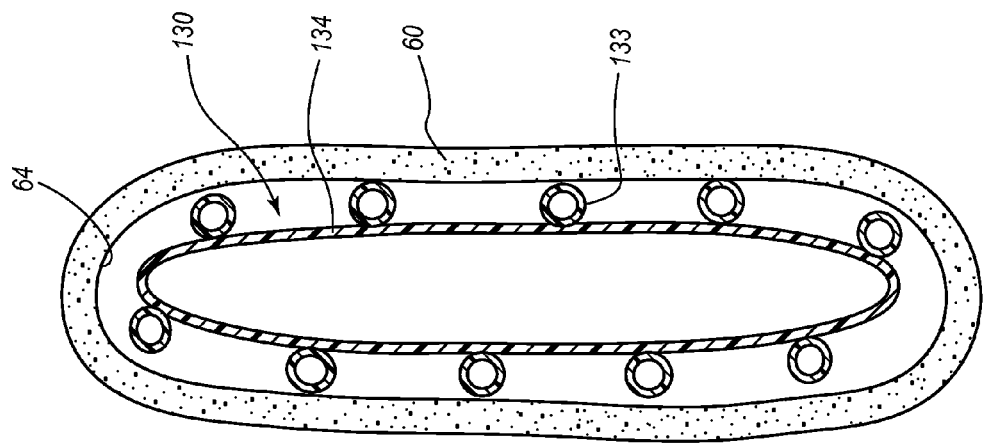
FIG. 10B is a cross-sectional view of the heat sensor of FIG. 1 within the esophagus of the patient taken along the view line 10B-10B of FIG. 10A.
Figure 10A:
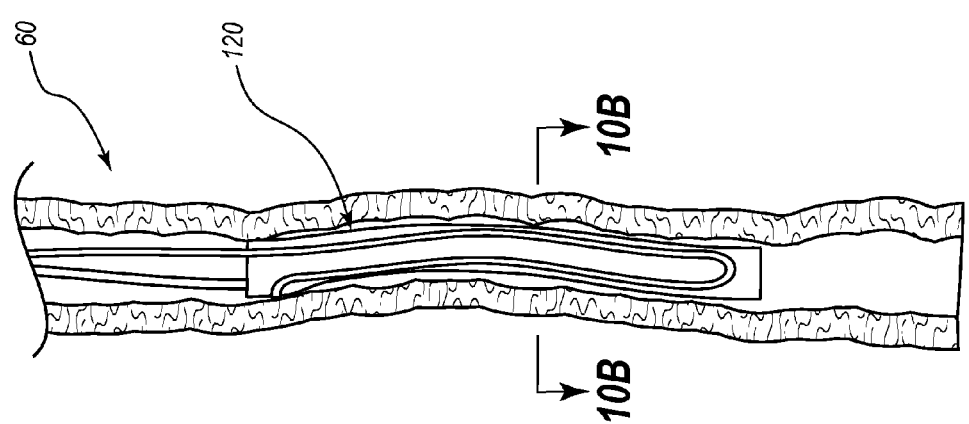
FIG. 10A is another elevation view of the heat sensor of FIG. 1 within the esophagus of the patient (shown in cross-section) after having been deployed within the esophagus and the inflation system removed from it, such that the sensor remains in the unpackaged or deployed state and is further in a compliance state so as to yield to movement of the esophagus.

FIGS. 10A and 10B illustrate a subsequent stage of placement of the sensor 120, in which the heat sensor 120 is in the desired position and is in an operational state, so as to be used during an ablation procedure. The inflation assembly 380 has been removed from an interior of the heat sensor 120, and the esophagus 60 has returned to its relaxed or natural orientation. In the illustrated embodiment, the support structure 130 is biased outwardly so as to maintain the conduit 133 in contact with and/or in close approximation to the inner surface 64 of the esophagus 60. In other or further embodiments, the support structure 130 and/or the conduit 133 may maintain contact with and/or close approximation via surface tension or other suitable methods or manners of adhesion, as discussed above. For example, although the substrate 134 is shown as being spaced from the inner surface 64 of the esophagus 60, in some embodiments, the substrate 134 may adhere to or otherwise contact the inner surface 64. In the illustrated configuration, the heat sensor 120 is still in the deployed or expanded state. However, as it is also now free to be moved by movement of the esophagus 60, or otherwise conform to the esophagus 60, it may also be referred to as being in a conformance, tracking, following, or according state. The support structure 130 and/or the conduit 133 may be sufficiently compliant or flimsy to remain in close proximity to the inner surface 64 of the esophagus substantially without deforming the esophagus. The heat sensor 120 may detect temperature changes and/or otherwise operate in manners such as described above.

In other embodiments, the inflation assembly 380 may remain at the interior of the heat sensor 120 during the ablation procedure. A pressure of the expansion fluid within the balloon 382 can be adjusted to maintain the heat sensor 120 in contact with the esophagus without expanding the esophagus. Rather, the pressure can be adjusted to a level at which the heat sensor 120 tracks the natural movement of the esophagus. Such a tracking state is similarly discussed below with respect to FIG. 12B.

In still other embodiments, the heat sensor 120 can be deployed within the esophagus 60 without the inflation assembly 380. For example, in some embodiments, the heat sensor 120 can be positioned within the esophagus 60 over a guidewire while being retained in the packaging sheath 377. Or in other or further embodiments, the heat sensor 120 can be selectively positioned within the esophagus 60 and released from the end of a cannula. In either case, whether upon removal of the sheath 377 or release from the cannula, a resilience of the wall material of the heat sensor 120 can cause the sensor to unroll, unfold, or otherwise expand and position itself against the wall 62 of the esophagus 60. In some embodiments, although the sensor 120 is sufficiently resilient to expand so as to conform to an inner surface of the esophagus 60, it may nevertheless track the movement of the esophagus and/or not substantially expand the esophagus.

FIGS. 11A and 11B illustrate another embodiment of a heat sensor 420, which is compatible with the heat sensing system 300 of FIG. 7A. The heat sensor 420 can function in a manner similar to the inflation assembly 380 discussed above, and thus may also be referred to as an inflation assembly. For example, the heat sensor 420 can include a support structure 430 similar to the support structure 130 discussed above, but which can also function in a manner similar to the balloon 182 discussed above. The support structure 430 can define at least a portion of a closed cavity 487 into which inflation fluid can be received to expand the support structure 430 and/or a heat sensing structure 440 into close proximity to (e.g., contact with) an inner wall of the esophagus. The heat sensor 420 can be assembled to a catheter 414, such as the catheter 314 discussed above. In the illustrated embodiment, the proximal and distal ends of the support structure 430 are attached to the catheter 414 and to a wire sheath 484 via proximal and distal fluid-tight seals 489, respectively. Accordingly, the closed cavity 487 can be defined by the support structure 430 and the wire sheath 484, which are sealed to each other via the fluid-tight seals 489.

Prior to the stage of insertion depicted in FIGS. 11A and 11B, the heat sensor 420 is in a packaged state within a packaging sheath, such as the packaging sheath 377 discussed above. In some embodiments, the wire sheath 484 is advanced over a guide wire 475 into the position shown in FIG. 11A. In the illustrated embodiment, the guide wire 475 is removed before progressing to subsequent stages of delivery. In other embodiments, the guide wire 475 may remain in place during greater amounts of the placement and/or heat sensing procedures. At the stage depicted in FIGS. 11A and 11B, an inflation fluid 486 is introduced into the cavity 487 and thereby expands the support structure 430 into contact and/or close proximity with the esophagus 60. The heat sensor 420 is thus in an expanded or deployed state. The guide wire 475 has been removed at this stage.

Figure 12B:
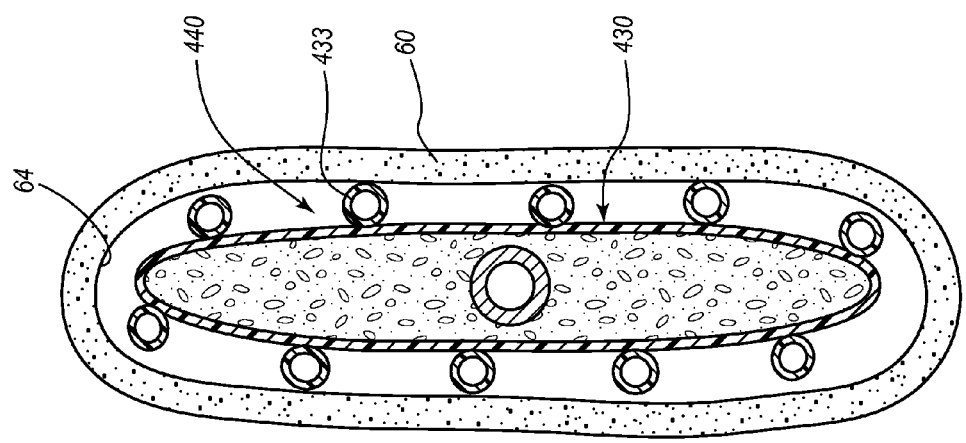
FIG. 12B is a cross-sectional view of the heat sensor of FIG. 11A taken along the view line 12B-12B in FIG. 12A.
Figure 12A:
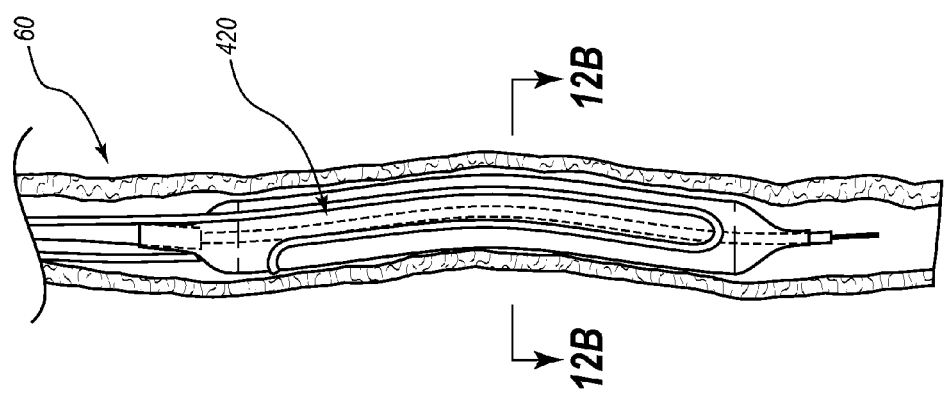
FIG. 12A is another elevation view of the heat sensor of FIG. 11A shown within the esophagus of a patient, wherein the heat sensor is in a compliance state in which the inflation fluid is at a lower pressure than that used to transition the heat sensor to the deployed state shown in FIG. 11A.

FIGS. 12A and 12B depict another stage of operation of the heat sensor 420 after it has been situated within the esophagus 60 of the patient. At this stage, the inflation fluid 486 remains within the support structure 430. However, the pressure of the inflation fluid 486 has been reduced, as compared with the inflation fluid at the stage of FIGS. 11A and 11B. The reduced pressure can allow the support structure 430 to comply with the natural configuration of the esophagus 60. Accordingly, the configuration shown in FIGS. 11A and 11B may be referred to as a conformance, tracking, following, or according state. As will be apparent from the discussion above regarding the inflation device 313, in some embodiments, the pressure of the inflation fluid 486 can be controlled by the inflation device 313. In some embodiments, the inflation device 313 can be controlled manually. In other embodiments, the inflation device 313 can be controlled by a controller in manners such as described above, and thus a pressure of the inflation fluid 486 can be controlled by the controller.

In some embodiments, expanding the support structure 430 by an amount sufficient to displace a portion of the esophagus 60, such as in the manner depicted in FIG. 11B, can aid in achieving a tight fit or contact between the support structure 430 and the esophagus. For example, this inflation stage can allow the support structure 430 to adhere to the inner surface 64 of the esophagus 60, such as by surface tension, by an adhesive coated on the exterior of the support structure 430, and/or in any other suitable manner. Thereafter, when the pressure of the inflation fluid 486 is reduced, the support structure 430 can maintain its close proximity with the inner surface 64 of the esophagus. Such a close proximity can aid with thermal transfer from the esophagus 60 to fluid flowing through a fluid passageway 441 defined by a conduit 433. In some arrangements, it can be desirable to ensure that the inflation pressure is reduced to an amount such as depicted in FIG. 12B prior to commencing ablation of the atrial wall 72, as the unexpanded or slack orientation of the esophagus 60 may provide greater spacing between the atrial wall 72 and the esophagus 60.

Figure 13:
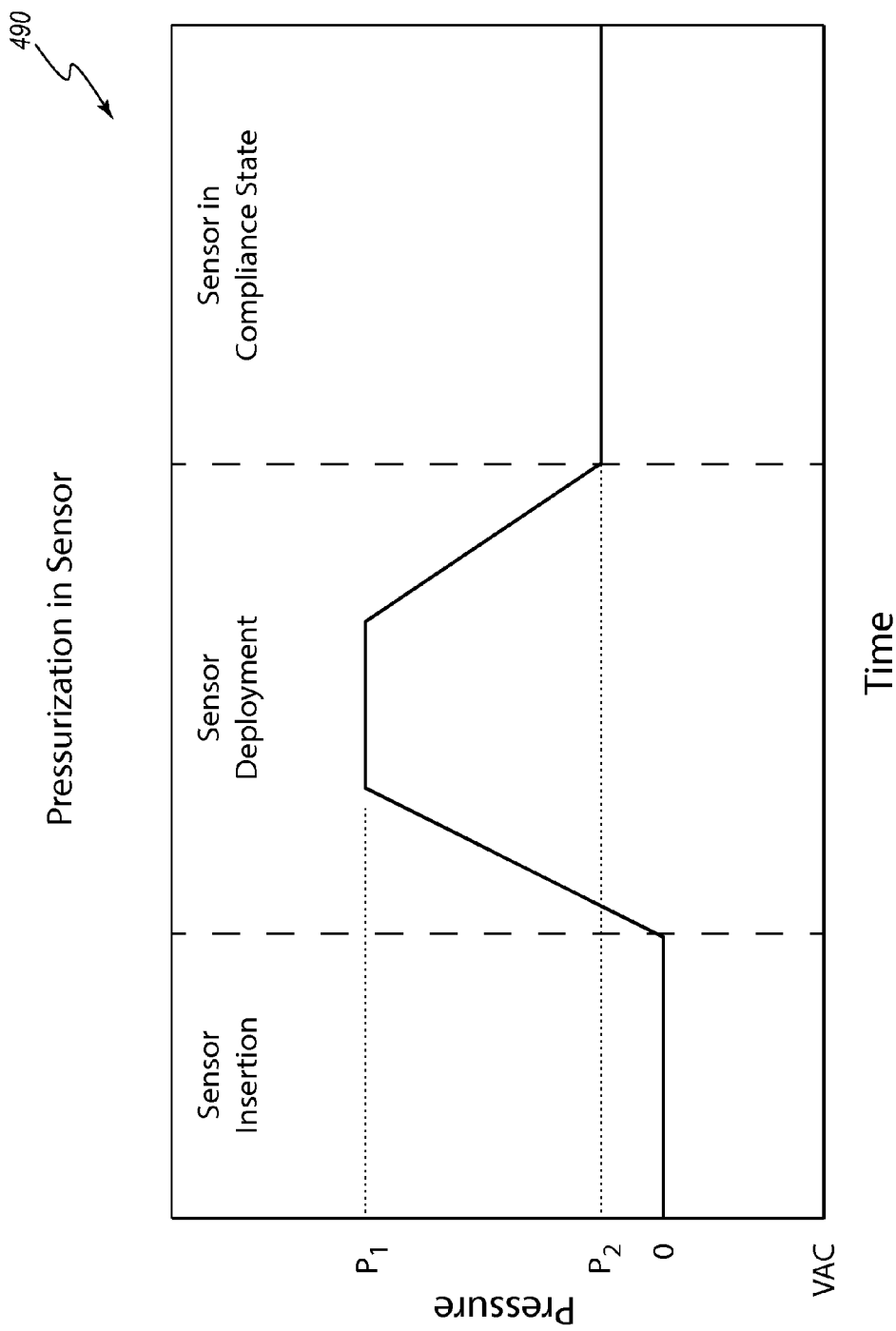
FIG. 13 is a plot of a pressure profile within the sensor of FIG. 11A during different stages of use.

FIG. 13 depicts a plot 490 of the pressure of the inflation fluid 486 as a function of time. Three different deployment stages are identified in the plot 490 as "Sensor Insertion," "Sensor Deployment," and "Sensor in Compliance State." During sensor insertion, only atmospheric pressure may be present within the support structure 430. During sensor deployment, which corresponds with FIGS. 11A and 11B, the inflation fluid 486 can increase the pressure to a value of $P_1$. Thereafter, when the heat sensor 420 is in the sensor compliance state (e.g., FIGS. 12A and 12B), the inflation fluid 486 can be reduced to a tracking pressure $P_2$. The tracking pressure $P_2$ can be sufficient to maintain contact between at least a portion of the support structure 430 and/or the heat sensing structure 440 and the esophagus wall, and yet not substantially deform the esophagus wall.

Figure 14:
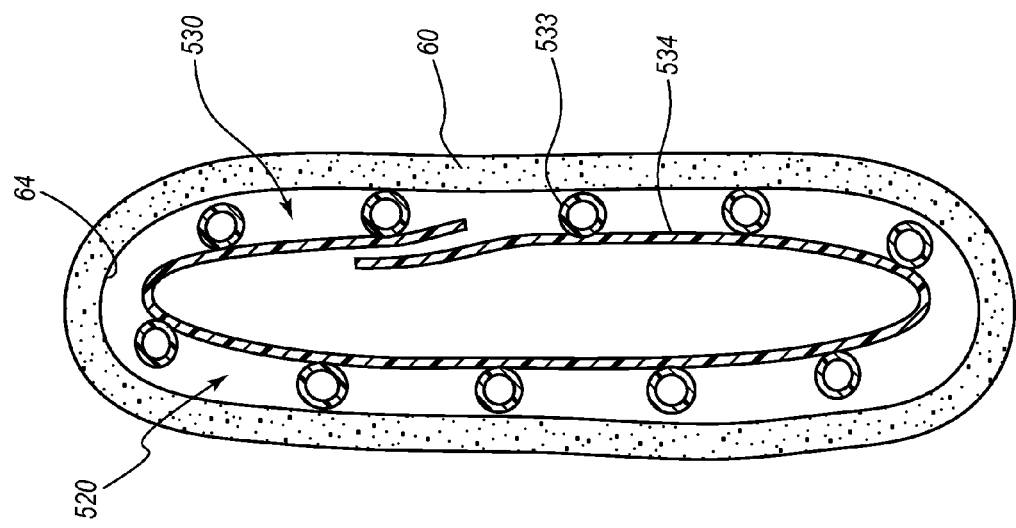
FIG. 14 is a cross-sectional view of another embodiment of a heat sensor that has been deployed within the esophagus of a patient.

FIG. 14 illustrates another embodiment of a heat sensor 520. The heat sensor 520 includes a support structure 530 that includes a substrate 534 and a heat sensing structure 540 that includes a conduit 533, which are substantially similar to the like-named features described above. However, when in a natural state, the substrate 534 is substantially flat or planar, rather than tubular. The conduit 533 likewise can be arranged in a pattern or shape that is substantially flat or planar. The heat sensor 520 may be rolled or coiled (e.g., into a tight spiral) about an inflation balloon (such as the inflation balloon 382 discussed above) and packaged within a packaging sheath (such as the packaging sheath 377 discussed above). The packaged heat sensor 520 may then be introduced into the esophagus of a patient in any suitable manner and expanded via the balloon in a manner such as discussed above.

In the deployment stage depicted in FIG. 14, the packaging sheath and the inflation balloon have been removed. In the illustrated embodiment, opposing side ends of the substrate 534 overlap one another when the sensor 520 has been positioned within the esophagus 60. Such an arrangement can allow for the heat sensor 520 to be used with any of a variety of patients whose anatomies differ, such that their esophagi define differently sized inner perimeters. For example, in smaller esophagi, the opposing side ends of the substrate 534 and/or the conduit 533 may overlap to a greater degree, whereas in larger esophagi, the opposing side ends of the substrate 534 may not overlap. In any of the foregoing instances, whether or not the opposing side ends of the substrate 534 overlap, the substrate 534 may be said to form a tube, sleeve, or sheath, which can extend along at least a portion of an inner perimeter of the esophagus. In various embodiments, the rolled, coiled, or curved substrate 534 may cover no less than about ¼, ⅓, ½, ⅔, or ¾ of, or no less than a majority of, the inner perimeter of the esophagus, and in instances where the side ends abut one another or overlap, can cover an entirety of the inner perimeter.

In instances where the side ends of the heat sensor 520 overlap, such as shown in FIG. 14, a width of the heat sensor 520, as measured between opposing side edges of the heat sensor 520, may exceed the value of the perimeter (e.g., the circumference) of the inner surface of the esophagus. In some arrangements, overlapping side ends of the heat sensor 520, such as those depicted in FIG. 14, may allow for the heat sensor 520 to yield more readily to movements of the esophagus 60, as compared with a closed tube. As can be appreciated from the drawings, in the illustrated embodiment, the heat sensor 520 is flexible about at least a longitudinal axis. In some embodiments, the heat sensor 520 is also flexible about axes that are perpendicular to the longitudinal axis, such that the heat sensor 520 can conform to any longitudinal curvature of the esophagus.

Figure 15:
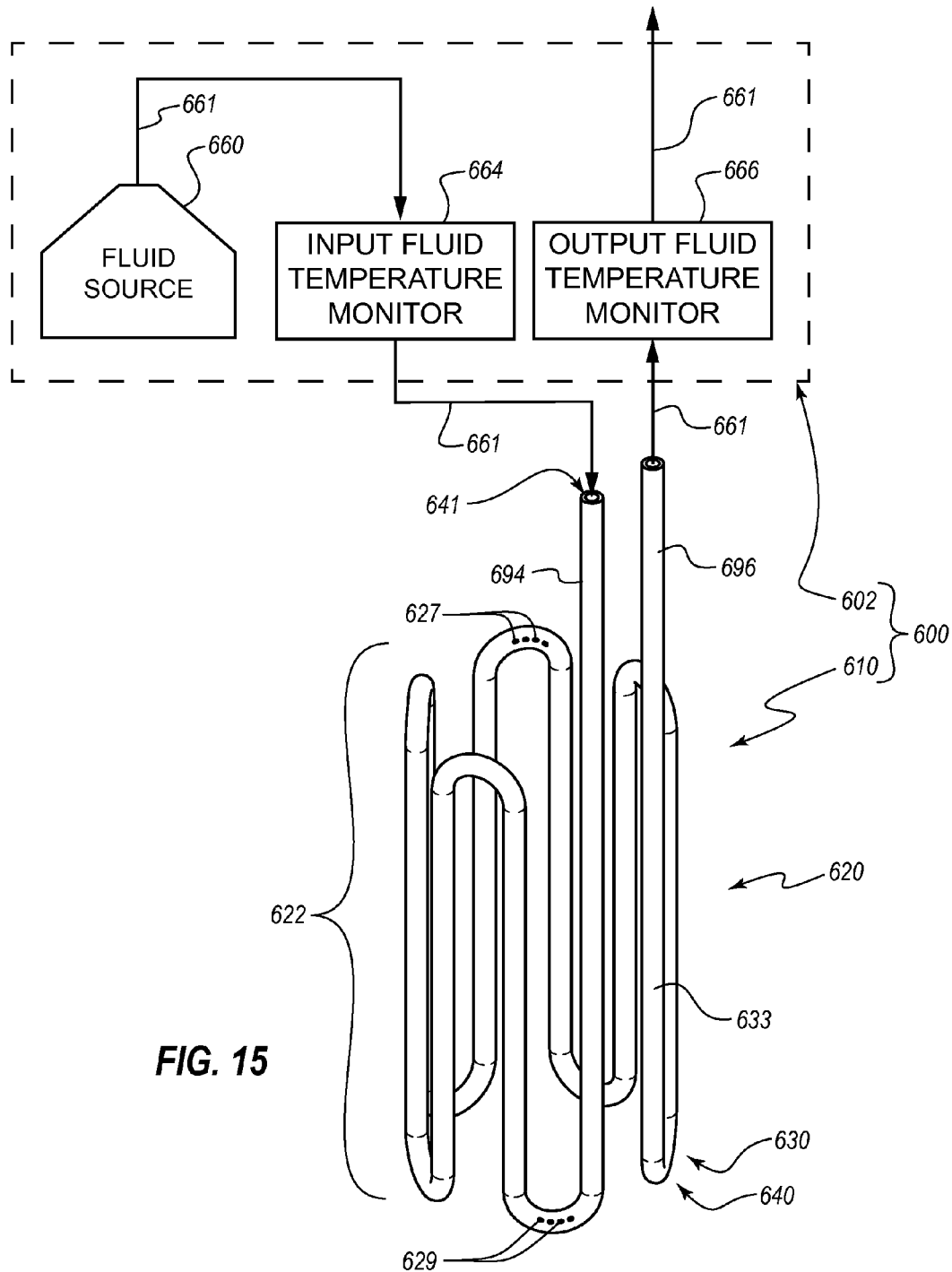
FIG. 15 is a schematic view of another embodiment of a heat sensing system and includes a perspective view of another embodiment of a heat sensor.

FIG. 15 illustrates another embodiment of a heat sensing system 600, which resembles the heat sensing system 100 in many respects. For example, the heat sensing system 600 includes a controller 602 that is coupled with a heat sensing assembly 610. The controller 602 may include, or otherwise be operatively or communicatively coupled with, a fluid source 660, an input fluid temperature monitor 664, and an output fluid temperature monitor 666. Unlike the system 100, however, in the illustrated embodiment, the heat sensing system 600 does not include a pump or a flowrate monitor.

In certain embodiments, the fluid source 660 may be pressurized. For example, the fluid source 660 can comprise a pressurized heat transfer fluid 661 (e.g., pressurized air or other gas), which may be circulated through a heat sensor 620. Although a flowrate monitor may be used in some arrangements, the illustrated embodiment does not include one. Instead, the flowrate may be calculated by knowing the resistance to fluid flow that is provided by the heat sensor 620 and all of the fluid connections, as well as the pressure of the fluid at the fluid source 660. For example, the fluid source 660 can comprise air or any other suitable gas at a known pressure, and the input fluid temperature monitor 664 and the output fluid temperature monitor 666 measure the heat added to the airflow as it passes through the circuit.

In the illustrated embodiment, the heat transfer fluid 661 is drained or vented at an exterior of the patient. For example, when the heat transfer fluid 661 comprises pressurized air, the air can be vented (e.g., to a surrounding environment or atmosphere) after it has passed through the system 600.

In certain embodiments, the system 600 may be operated in the same manner as the system 100. For example, in some embodiments, the system 600 may be operated in a manner that would yield a plot such as the plot 250 described above with respect to FIG. 7. Moreover, any suitable heat sensor may be used with any of the systems 100, 600. For example, any of the heat sensors 120, 420, 520, 620 may be used with either of the systems 100, 600. Other heat sensors described below are also suitable for use with either of the systems 100, 600.

In the illustrated embodiment, the heat sensor 620 that is similar to the heat sensor 120, and can include a single fluid passageway or channel 641 defined by a tube or conduit 633 that defines a switchback or serpentine pattern. The serpentine pattern may extend up and down along a longitudinal length of the sensor 620, and may encompass at least a portion of a lateral perimeter of the sensor 620. The sensor 620 can further include an inlet branch 694 at one end of the conduit 633 and an outlet branch 696 at an opposite end of the conduit 633.

Figure 16:
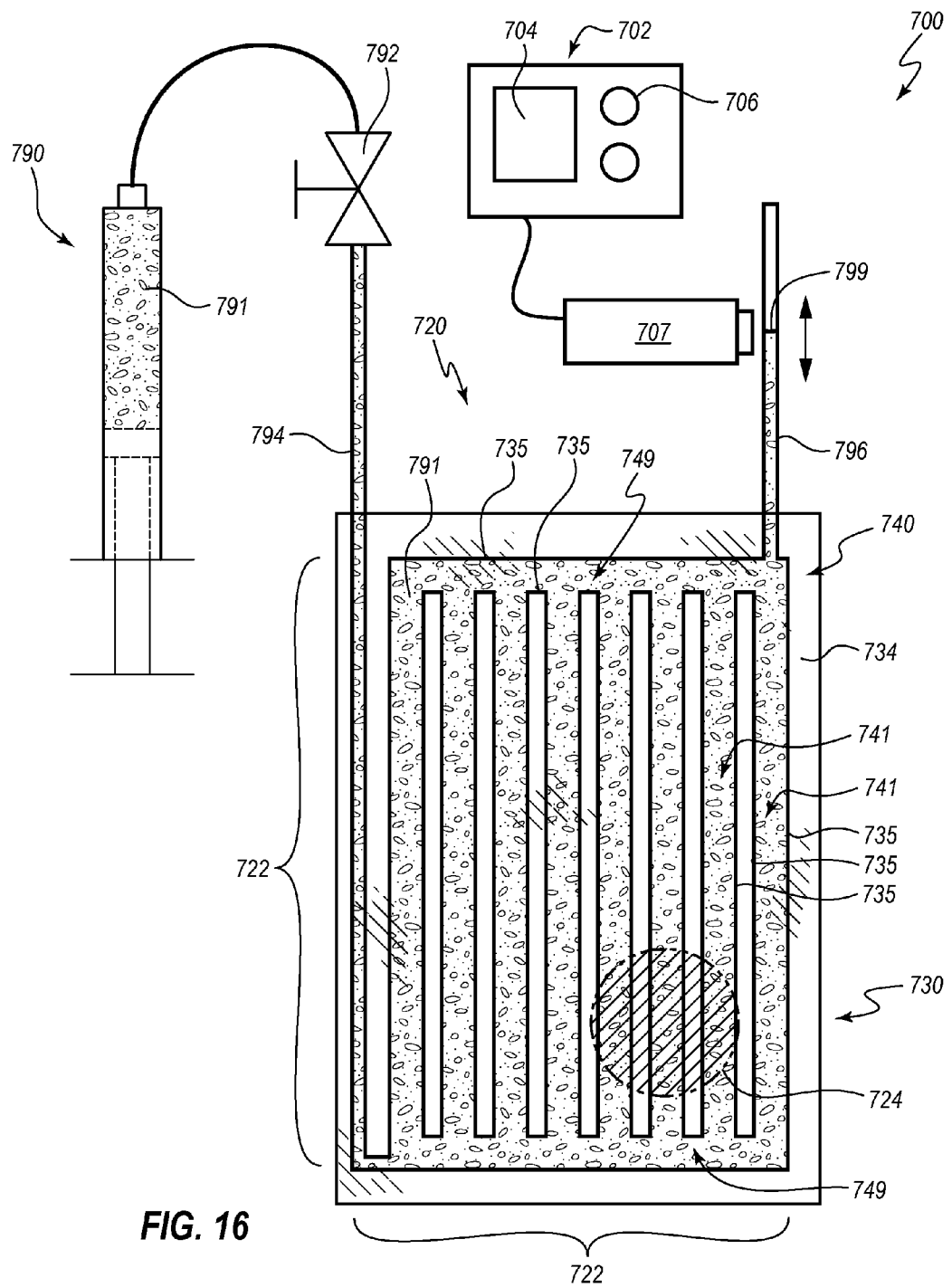
FIG. 16 is a schematic view of another embodiment of a heat sensing system and includes an elevation view of another embodiment of a heat sensor.

The conduit 633 can function as both a support structure 630 and a heat sensing structure 640. Stated otherwise, the conduit 633 may have sufficient structural integrity and/or be otherwise configured such that a separate substrate is not used with the conduit 633. In various embodiments, the support structure 630 may be rigid, whereas in other embodiments it may be resiliently flexible. Further, the structure 630 may be flexible about one or more axes, in manners such as described above. In certain embodiments in which the support structure 630 is rigid, the support structure 630 can be configured to maintain its shape independent of external forces (e.g., from the esophagus) or internal forces (e.g., due to expanding or contracting temperature-sensitive fluid). Certain of such embodiments can be particularly well suited for use in heat sensing systems such as the heat sensing system 700 discussed hereafter with respect to FIG. 16, given that a volume of generally stationary fluid within the rigid structure would be less susceptible to movements due to a changing shape or volume of the conduit 633. Other embodiments may be used with flowing fluid systems, such as the system 600 in which the heat sensor 620 is presently shown (as well as the heat sensing system 100). It may be said that the support structure 630 defines and/or carries the fluid passageway 641.

In certain embodiments in which the support structure 630 is resiliently flexible, the support structure 630 may be more capable of yielding to, or tracking, the natural movements of the esophagus while having sufficient structural integrity to maintain or return to a natural configuration when external stresses are removed from the support structure 630. In certain of such embodiments, the conduit 633 can comprise a resilient biocompatible plastic material. In other or further embodiments, the conduit 633 can comprise a shape memory alloy. The resilient conduit 633 may be readily deployed within the esophagus in any suitable manner, such as those discussed above. For example, in some embodiments, the heat sensor 620 may initially be in a compressed, packaged, or delivery state, and in further embodiments, may be retained in that state via a delivery sheath. After positioning within the esophagus, the conduit 633 may be transitioned to an expanded state and may be in contact with or otherwise in close proximity to the inner wall of the esophagus. Certain of such flexible embodiments may be less desirable in a heat sensing system such as that discussed hereafter with respect to FIG. 16, as changes in the shape of or the amount of expansion or compression of the conduit 633 could affect a level of a temperature-sensitive fluid within the tube. In some arrangements, this fluctuation in the fluid level due to mechanical deformations of the resilient tube 633 could obfuscate fluid level fluctuations that are due to a change in the temperature of the fluid. However, in some instances, the moveable or resilient conduit 633 may be particularly well suited for a different type of heat sensing system in which fluid levels are not monitored, such as embodiments of the heat sensing systems 100, 600.

Whether it is rigid, resiliently flexible, or has some other structural integrity (e.g., high compliance, such as that of certain embodiments of the conduit 933 discussed below), the conduit 633 can function as a heat sensing structure 640 similar to other heat sensing structures described herein. For example, in some embodiments, temperature-sensitive fluid 661 may be introduced into the conduit 633, and the heat sensor 620 may function in manner such as described above with respect to the heat sensors 120, 420, 520. For example, in some embodiments, the portion of the conduit 633 that is distal to the inlet and outlet conduits 694, 696 can define a heat sensing region 622 capable of sensing heating at any position therein (e.g., at a temperature alteration zone, such as the zone 743 described hereafter). In some embodiments, the conduit 633 can include one or more imaging markers 627, 629, such as the imaging markers 127, 129 discussed above.

FIG. 16 illustrates another embodiment of a heat sensing system 700. The system can include a monitor 702, which can include any suitable display 704 and actuators 706. The monitor 702 can be configured to communicate with a photosensor 707 or other suitable device configured to monitor a level 799 of a temperature-sensitive fluid 791, as further discussed below.

The heat sensing system 700 can include a heat sensor 720, which can include a support structure 730 and a heat sensing structure 740. In the illustrated embodiment, the support structure 730 includes a front panel, or substrate 734, and a rear panel, or superstrate 732 (shown in FIG. 18). The substrate 734 is clear in the present embodiment, such that portions of the heat sensor 720 that are beneath the substrate 734 are visible. A series of fluid passageways or channels 741, 749 can be positioned between the substrate 734 and the superstrate 732. In the illustrated embodiment, the outer contours of the fluid channels 741, 749 are defined at least in part by fluid-tight seams 735 (e.g., ultrasonic welds, heat seams, etc.) that join the substrate 734 to the superstrate 732. Other suitable methods for forming the fluid channels 741, 749 are also possible.

The support structure 730 may be flexible about at least one axis. For example, although the support structure 730 is shown in a substantially planar configuration in FIG. 16, the support structure 730 may be curved or curled about a longitudinal axis so as to be positioned within the esophagus (e.g., in a manner similar to that depicted in FIG. 14). In other embodiments, the support structure 730 may be rigid or relatively inflexible. In certain of such embodiments, the esophagus may be collapsed about opposing faces of the support structure 730, such as described below with respect to FIGS. 17A-18. The support structure 730 may comprise any suitable material, such as any of the materials described above with respect to the support structure 130.

In the illustrated embodiment, the heat sensing structure 740 comprises the fluid channels 741, 749, and may be referred to as a grid, pattern, or manifold. The fluid channels 741 are substantially parallel to each other and run longitudinally, and separate manifold fluid channels 749 are positioned at the upper and lower ends of the fluid channels 741 so as to interconnect them. An inlet conduit 794 and an outlet conduit 796 can extend from any of the fluid channels 741, 749, and in the illustrated embodiment, the inlet and outlet conduits 794, 796 extend from a lower fluid channel 749 and an upper fluid channel 749, respectively, at opposite sides of the support structure 730.

The inlet conduit 794 can selectively communicate with any suitable injection device 790 in any suitable manner. In the illustrated embodiment, the injection device 790, which is a syringe, is configured to selectively deliver temperature-sensitive fluid 791 through a valve 792, when the valve is open, so as to fill the fluid channels 741, 749 prior to use of the heat sensor 720. When the valve 792 is closed, fluid is prevented from moving from the inlet conduit 794 back through the valve 792.

The outlet conduit 796 can include a column of the temperature-sensitive fluid 791 that is permitted to rise and fall therein. A level 799 of the column can move up or down depending on the temperature of the fluid 791, as indicated by the double-headed arrow. The photosensor 707 or other suitable device can be used to monitor the level 799.

The heat sensing structure 740 can define a heat sensing region 722. Similar to the discussion above with respect to the heat sensing structure 140, the heat sensing structure 740 can be configured to sense a change in temperature within a temperature alteration zone 724, where at least a portion of the temperature alteration zone 724 is within the heat sensing region 722. Stated otherwise, the heat sensing region 722 can define a large area for sensing temperature changes, and temperature changes that are effected in even a small portion of this area can be detected.

In the illustrated embodiment, when heating occurs within the temperature alteration zone 724, the temperature-sensitive fluid 791 can expand relative to the support structure 730, which can cause the fluid level 799 to rise. In some embodiments, the heat sensing system 700 may be better configured for monitoring a change in temperature at any position within the heat sensing region 722, as opposed to determining at which position within the heat sensing region 722 the change is occurring or determining specific temperatures at various regions within the heat sensing region 722. However, in other embodiments, if desired, multiple manifolds or channel systems, each with a separate outlet conduit 796 and fluid level 799 indicator, can be used to determine the portion of the heat sensing region 722 that is undergoing a temperature change, and possibly to determine the temperature of that portion of the sensing region 722.

Figure 17C:
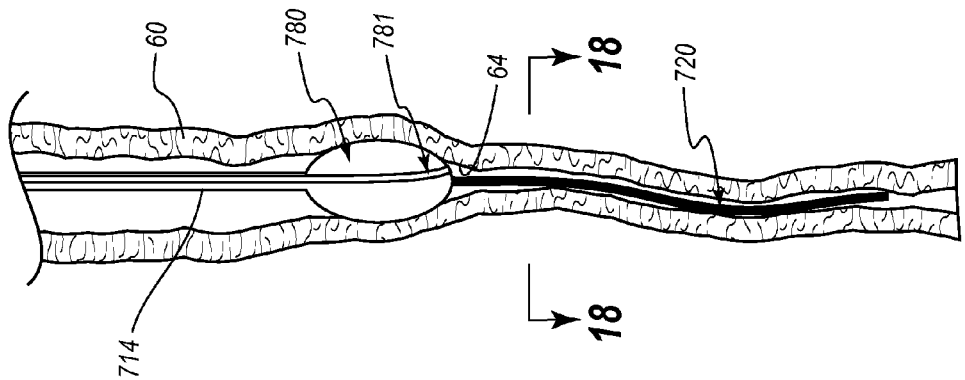
FIG. 17C is another cross-sectional view of the portion of the heat sensing system of FIG. 17A showing the esophagus collapsed into contact and/or close proximity to the heat sensor.
Figure 17B:
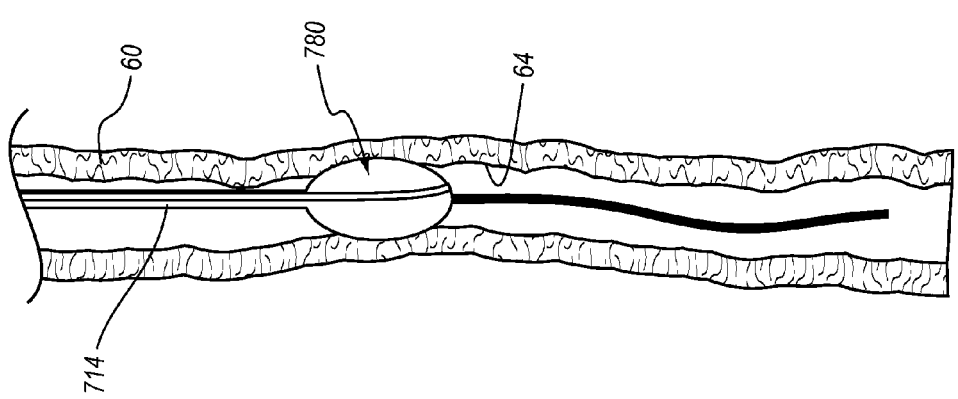
FIG. 17B is another cross-sectional view of the portion of the heat sensing system of FIG. 17A showing a balloon inflated into contact with the inner surface of the esophagus.

In some embodiments, the panels (e.g., the substrate 724 and the superstrate 722) of the support structure 730 can be locally rigid so as to resist deformation due to externally applied forces (e.g., from the esophageal wall) or internal forces (e.g., from the temperature-sensitive fluid 791). Such local rigidity can prevent the fluid channels 741, 749 from having variable volumes, and can aid in ensuring that any change in the level 799 is due to a sensed change in temperature, rather than a resizing of the fluid channels 741, 749. In some embodiments, the panels may be substantially planar, such as shown in FIGS. 16 and 18. In some arrangements, the esophageal wall may be brought into contact or close proximity with the substantially planar panels in any suitable manner, such as, for example, those discussed below with respect to FIGS. 17A-18. In other embodiments, the panels may be cylindrical (such as shown in FIG. 19), or may be any other suitable shape. For example, in some embodiments, the support structure 730 may have end-to-end flexibility so as to be deformable about at least one axis. For example, the support structure 730 can be deformable relative to at least a longitudinal axis, which longitudinal axis can be aligned with (or positioned parallel to) a longitudinal axis defined by the esophagus, such that the support structure 730 can conform to a shape of the esophageal wall about a periphery thereof (e.g., in a manner such as illustrated in FIG. 10B).

In some embodiments, the heat sensor 720 can be used in a different heat sensing system, such as the systems 100, 600. For example, in some embodiments, fluid may flow through the support structure 730, rather than remaining substantially stationary therein (e.g., for purposes of determining expansion or contraction of the fluid).

Figure 17A:
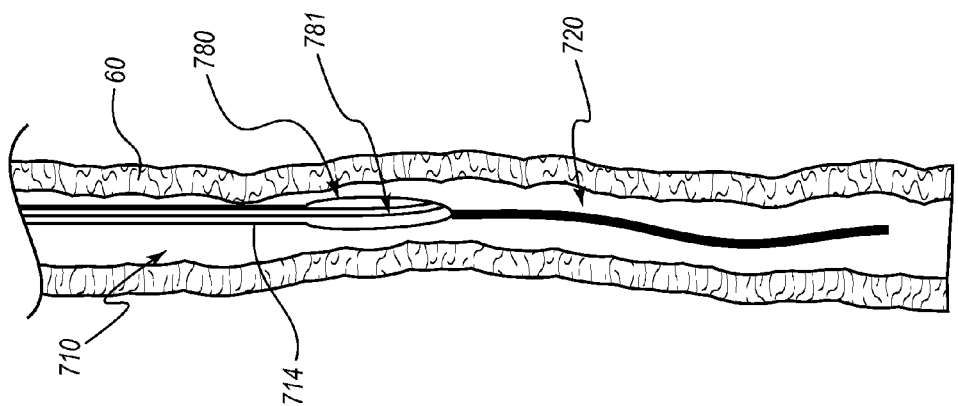
FIG. 17A is a cross-sectional view of a portion of another embodiment of a heat sensing system that includes a heat sensor shown positioned within the esophagus of a patient, wherein the heat sensing system includes an esophagus collapsing feature.
Figure 18:
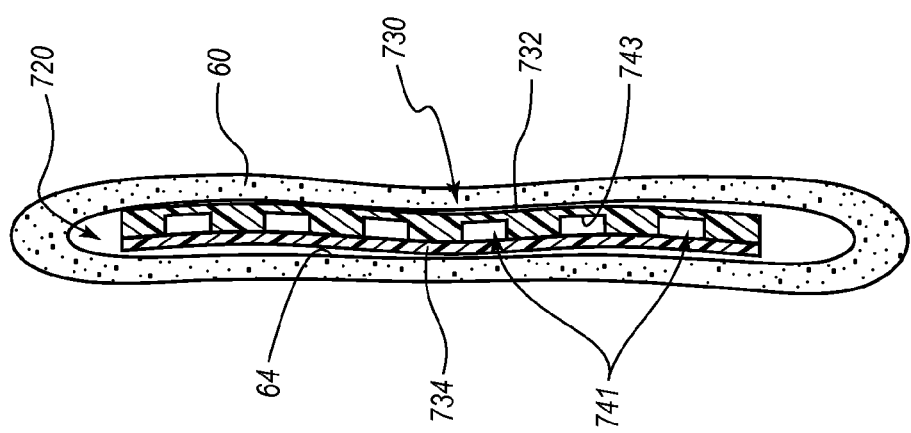
FIG. 18 is a cross-sectional view of the esophagus collapsed into contact and/or close proximity to the heat sensor taken along the view line 18-18 in FIG. 17C.
Figure 19:
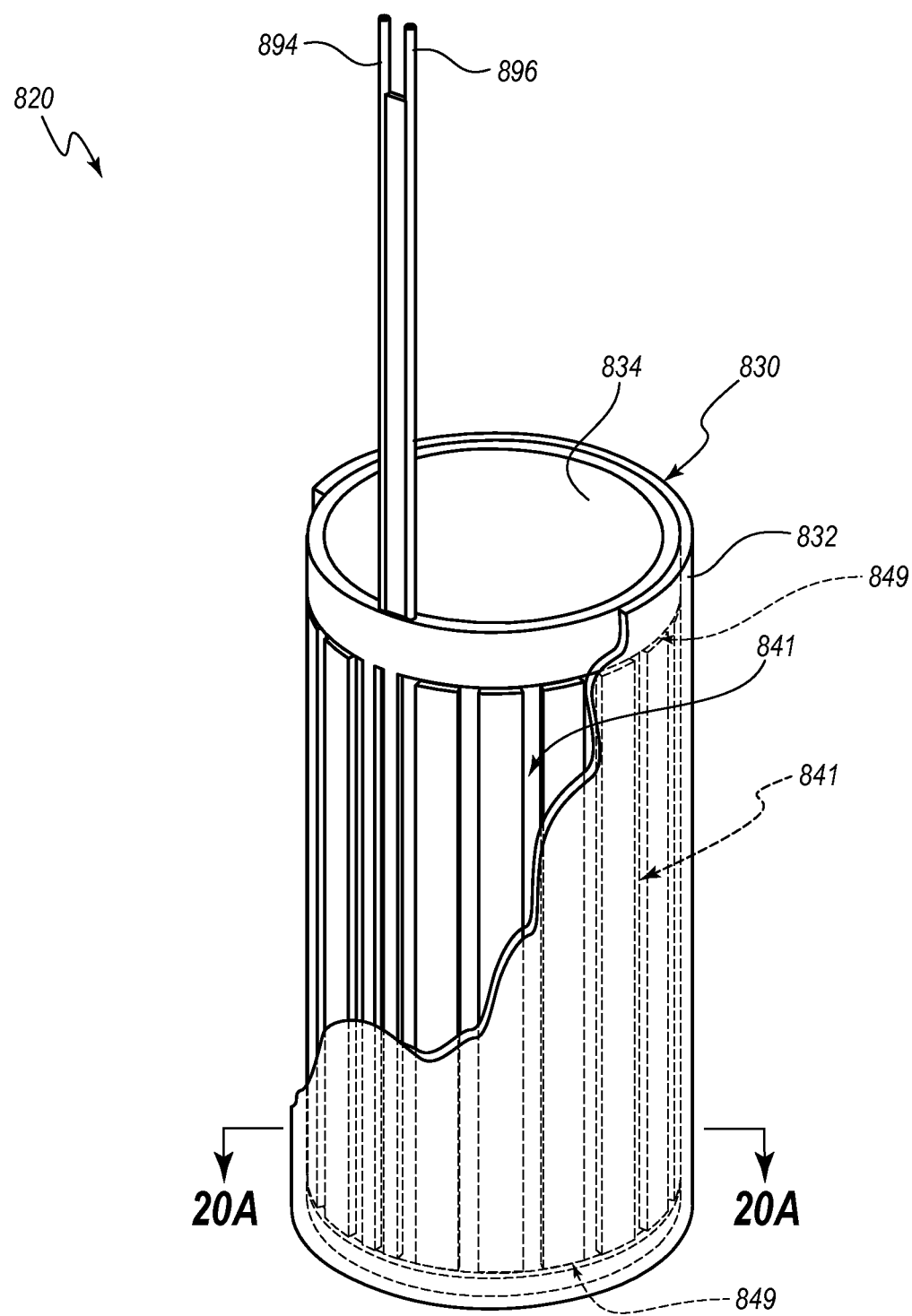
FIG. 19 is a perspective view of another embodiment of a heat sensor.

FIGS. 17A-18 illustrates that in some embodiments, the heat sensor 720 can be included at the distal end of a heat sensing assembly 710 that is configured to collapse the esophagus into proximity to the heat sensor 720. Such an esophageal collapsing system can be employed with any suitable heat sensing system and/or heat sensor described herein. The heat sensing assembly 710 is shown within the esophagus 60 of a patient at different stages of deployment. As previously noted, the heat sensing assembly 710 can include a heat sensor of any suitable variety, and the heat sensor 720 is depicted in the illustrated embodiment. As discussed above, in some arrangements, the heat sensor 720 may include a support structure 730 that defines a substantially planar or flat configuration when deployed within the esophagus, rather than being curled into a generally tubular shape so as to expand into close proximity to the esophageal wall. Accordingly, in some embodiments, the support structure 730 may be thicker and/or less pliable (e.g., more rigid) than the curled support structures of certain embodiments of the heat sensor 720. In other embodiments, the support structure 730 may be pliable in manners such as discussed above, and may readily comply with, conform to, or track a shape of the esophagus. As shown in FIG. 18, in the illustrated embodiment, the support structure 730 includes two layers 732, 734 that are joined together so as to define fluid channels 741.

With continued reference to FIG. 18, in some embodiments, the channels 741 are at least partially defined by a series of grooves 743 in one or more of the superstrate 732 and the substrate 734. The superstrate 732 and the substrate 734 can be laminated, adhered, welded, or otherwise attached to each other. In the illustrated embodiment, the substrate 734 and the superstrate 732 are defined by separate pieces of material that are joined together. In other embodiments, the substrate 734 and the superstrate 732 can be formed of a unitary piece of material that is folded or otherwise formed in a manner that encapsulates the channels 743.

With reference again to FIGS. 17A-17C, the heat sensing assembly 710 can include any suitable device or system for collapsing the esophagus about the heat sensor 720. Collapsing the esophagus 60 so as to bring the inner wall 64 into close contact and/or close proximity with the heat sensor 720 can increase thermal transfer between the wall and the heat sensor 720. In some instances, collapsing the esophagus 60 may space the esophageal wall further from the heart, which may also reduce heating of the wall during an ablation procedure. Such an arrangement may, in some instances, facilitate construction of the heat sensor 720, given that a larger range of pliability or rigidity may be suitable for the support structure 730 as compared with some other arrangements, as previously discussed. Such a system may be described as being configured to collapse the esophagus into contact or close proximity to the heat sensor 720, rather than expanding or otherwise deploying the heat sensor 720 into contact or close proximity to the esophagus.

In the illustrated embodiment, the device for collapsing the esophagus comprises an inflatable balloon 780 having an evacuation lumen 781. A proximal portion of the evacuation lumen 781 is housed in a catheter 714. Although the evacuation lumen 781 is shown extending through the inflatable balloon 780 in the illustrated embodiment, the evacuation lumen 781 can be separate from the balloon 780 in other embodiments. In some embodiments, the catheter 714 further includes a fluid path (not shown), such as the fluid path 315 discussed above, through which an inflation fluid can be delivered to and removed from the balloon 780. In further embodiments, the catheter 714, or a separate catheter, can house fluid channels to and from the heat sensor 720.

As shown in FIG. 17A, the heat sensing assembly 710 can be introduced into the esophagus 60 with the balloon 780 in a collapsed state. Once the heat sensor 720 is in a desired position, inflation fluid may be used to expand the balloon 780 into contact with the inner wall 64 of the esophagus 60, as shown in FIG. 17B. The contact may provide a fluid-tight seal. As shown in FIG. 17C, air and/or fluids about heat sensor 720 can be evacuated via the evacuation lumen 781 to bring the esophagus into contact and/or close proximity to the heat sensor 720. In the illustrated embodiment, a single balloon 780 is used in the evacuation/collapsing procedure, and the balloon 780 is positioned proximally relative to the heat sensor 720. In other embodiments, the balloon 780 may be positioned distally relative to the heat sensor 720. In still other embodiments, the heat sensing assembly 710 may include two balloons that are positioned proximally and distally relative to the heat sensor 720. In such embodiments, the portion of the esophagus that is between the expanded balloons can be evacuated.

Figure 20A:
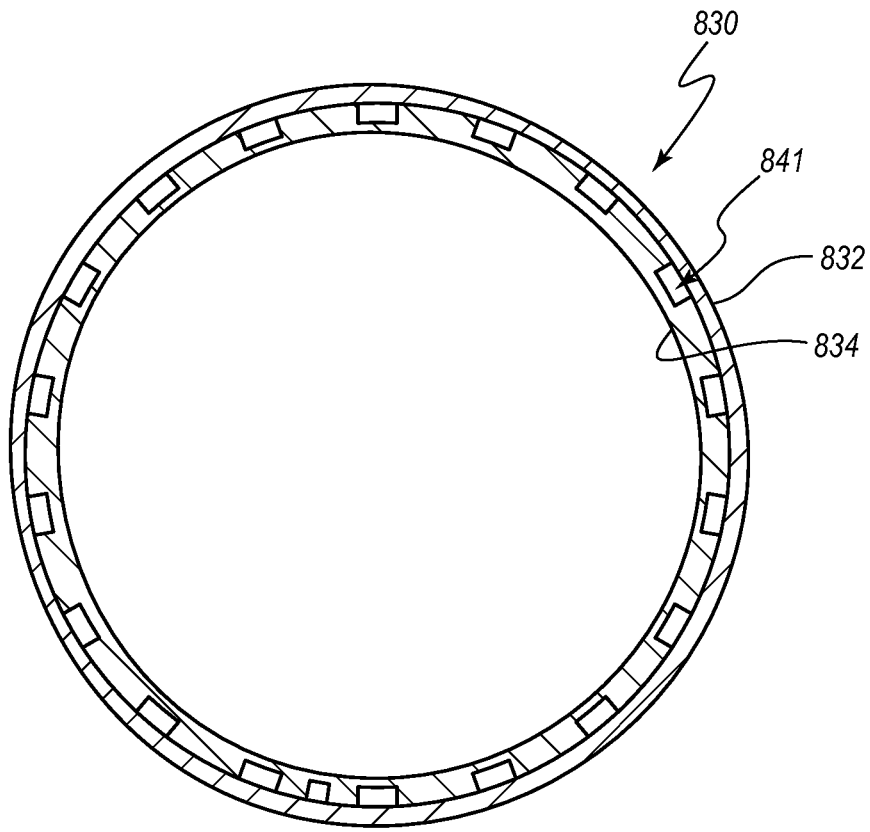
FIG. 20A is a cross-sectional view of the heat sensor of FIG. 19 taken along the view line 20A-20A, wherein the heat sensor is in an expanded state.
Figure 20B:
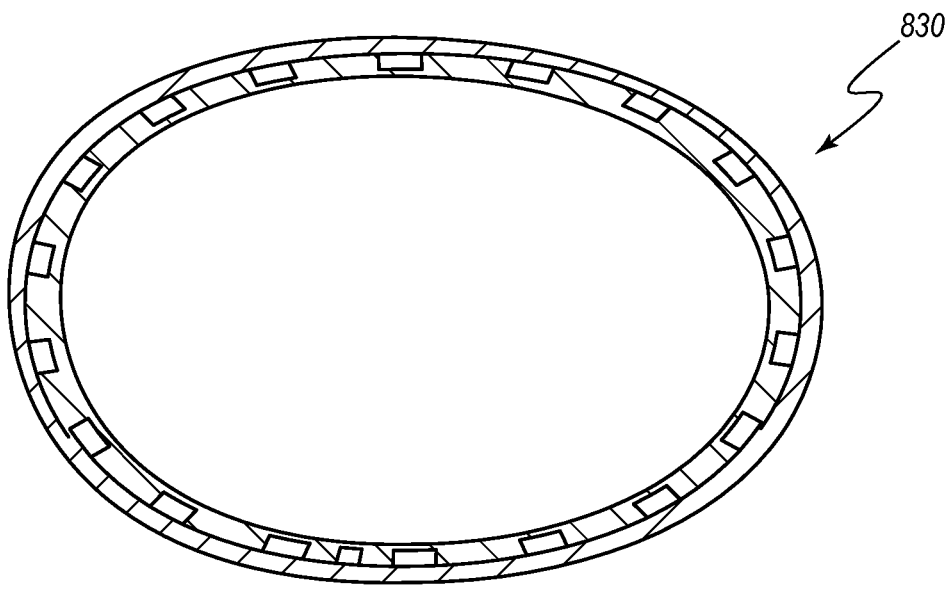
FIG. 20B is another cross-sectional view of the heat sensor of FIG. 19 similar to the view shown in FIG. 20A, wherein the heat sensor is shown in a compressed or tracking state.

FIGS. 22-23B illustrate another embodiment of a heat sensor 820 similar to the heat sensor 720. Like the heat sensor 720, the heat sensor 820 includes an inlet conduit 894 and an outlet conduit 896 that are in fluid communication with a series of fluid passageways or channels 841, 849. The channels 841, 849 can be formed as spaces between an outer panel, or outer layer 832 and an inner panel, or inner layer 834 of material that forms a flexible support structure 830. However, unlike the support structure 730, the support structure 830 forms a closed loop (see FIG. 20A). As shown in FIG. 20A, the support structure 830 can be naturally biased toward a substantially cylindrical orientation. However, the support structure 830 may be readily transitioned to orientations that conform to the interior of the esophagus, as illustrated in FIG. 20B. More compliant or limp arrangements, such as described above, are also possible for the support structure 830.

FIGS. 21A-22B depict another embodiment of a heat sensor 920 that is compatible with various heat sensing systems disclosed herein. For example, the heat sensor 920 may be operatively coupled with any of the controllers 102, 302, 602, 702 and associated components discussed above. In some embodiments, the heat sensor 920 includes a tube or conduit 933 having an inlet branch 994 and an outlet branch 996. The heat sensor 920 can be configured to readily conform to the inner wall of the esophagus. For example, the heat sensor 920 can be extremely compliant, or stated otherwise, can have very little rigidity. In the illustrated embodiment, the conduit 933 has a structural integrity resembling a thread, a string, or wet noodle. That is, the conduit 933 can be readily moved into any desired orientation, and in some embodiments, may not have a significant intrinsic orientation bias. For example, the conduit 933 may readily respond to external forces (e.g., gravity, surface tension, adhesion forces) without internally counteracting those forces.

Figure 22A:
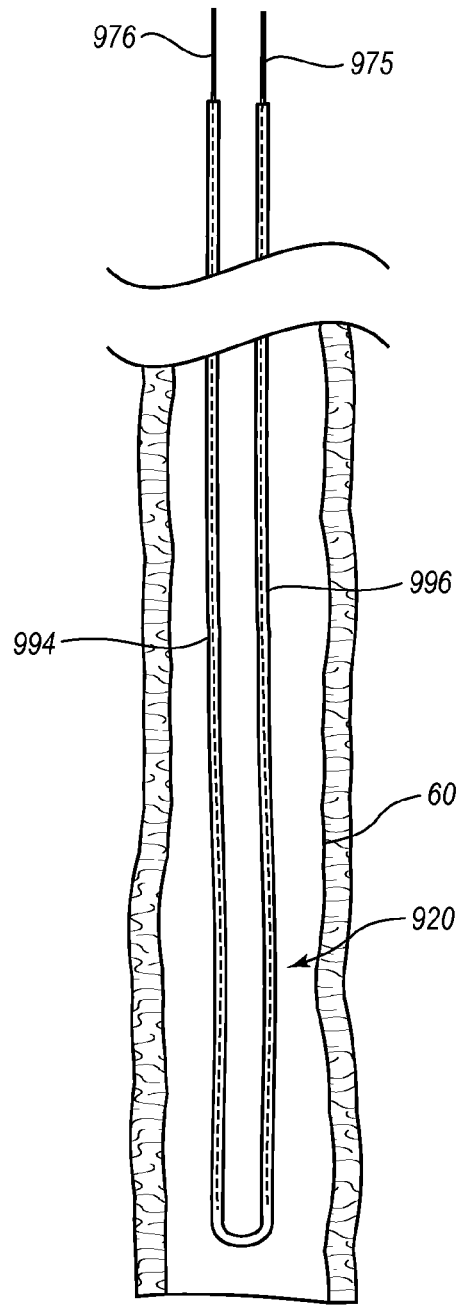
FIG. 22A is an elevation view of the heat sensor of FIG. 21A being introduced into the esophagus of a patient.

With reference to FIG. 22A, in some embodiments, the heat sensor 920 has an outer diameter and outer perimeter that are significantly smaller (e.g., smaller by a factor of no less than 5 times) than the inner diameter and inner perimeter of the esophagus. The heat sensor 920 can be introduced into the esophagus 60 of a patient over one or more guide wires 975, 976. The guidewires 975, 976 may support the conduit 933 and can extend to a distal position. A distal portion of the conduit 933 can extend between the distal ends of the guidewires 975, 976. In this orientation, during early stages of positioning, the guidewires 975, 976 and the conduit 933 can substantially define an elongated U-shape. The U-shaped conduit 933 can have two branches (e.g., the branches 994, 996).

Figure 22B:
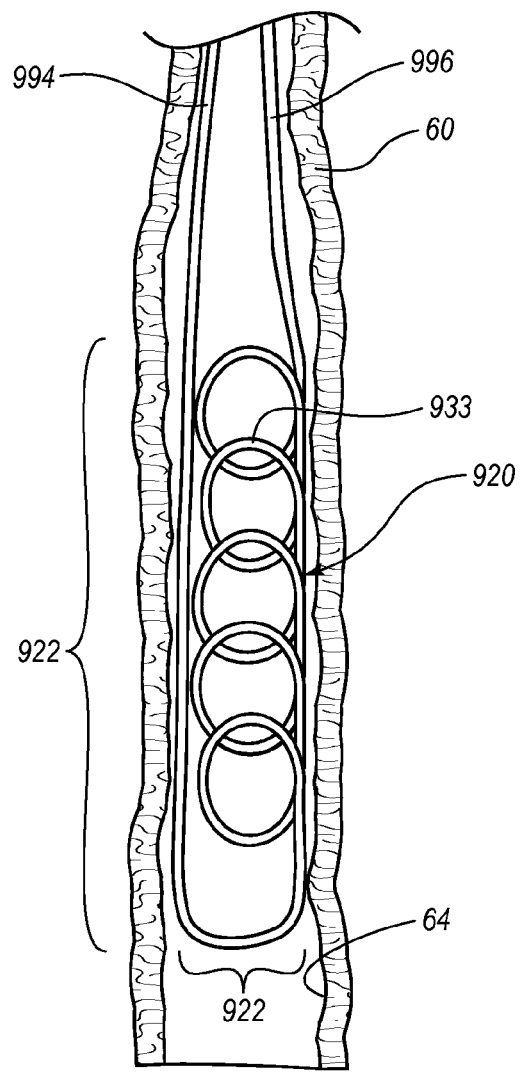
FIG. 22B is another elevation view of a later stage of the heat sensor of FIG. 21A being positioned within the esophagus of the patient.

As shown in FIG. 22B, the guidewires 975, 976 can position a portion of the conduit 933 at a distal region of the esophagus and can be retracted from the esophagus 60. The guidewire 976 can be present in the first branch of the conduit 933 (e.g., the inlet branch 994) as the guidewire 975 is retracted from the second branch of the conduit 933. As the guidewire 975 is retracted, it may trace out a generally spiral pattern relative to the esophageal wall 64. As the distal tip of the guidewire 975 is further retracted in the proximal direction, segments of the conduit 933 can successively adhere and conform to the esophageal wall 64, such as by surface tension. The guidewire 976 may then be retracted from the first branch of the conduit 933.

When the guidewires 975, 976 are fully retracted from the heat sensor 920, the conduit 933 can define a heat sensing region 922 that extends along a longitudinal length of the esophagus 60 and extends along an inner periphery of the esophagus 60. In some arrangements, a practitioner can control a density of the conduit 933 within the heat sensing region 922. For example, in some instances where greater sensitivity within the heat sensing region 922 may be desired for a given conduit 933, the conduit 933 may be spiraled tightly such that adjacent loops are relatively close together. In other instances where less sensitivity within the heat sensing region 922 may be sufficient for the same conduit 933, the conduit 933 may have a looser spiral, such that adjacent loops are further apart.

In other embodiments, the conduit 933 may be applied to the esophageal wall 64 in any suitable arrangement. For example, rather than a generally helical shape, such as shown in FIG. 22B, the conduit 933 may be applied in any other regular pattern, such as, for example, a serpentine pattern. In still other embodiments, an irregular shape or pattern may be used. For example, the conduit 933 may be permitted to assume a jumbled or squiggled shape that covers a swath of the inner esophageal wall 64. In various embodiments, the conduit 933 may be situated within the esophagus so as to extend circumferentially around no less than about ¼, ⅓, ½, ⅔, or ¾ of, or no less than a majority of, an inner perimeter of the esophagus.

Figure 21A:
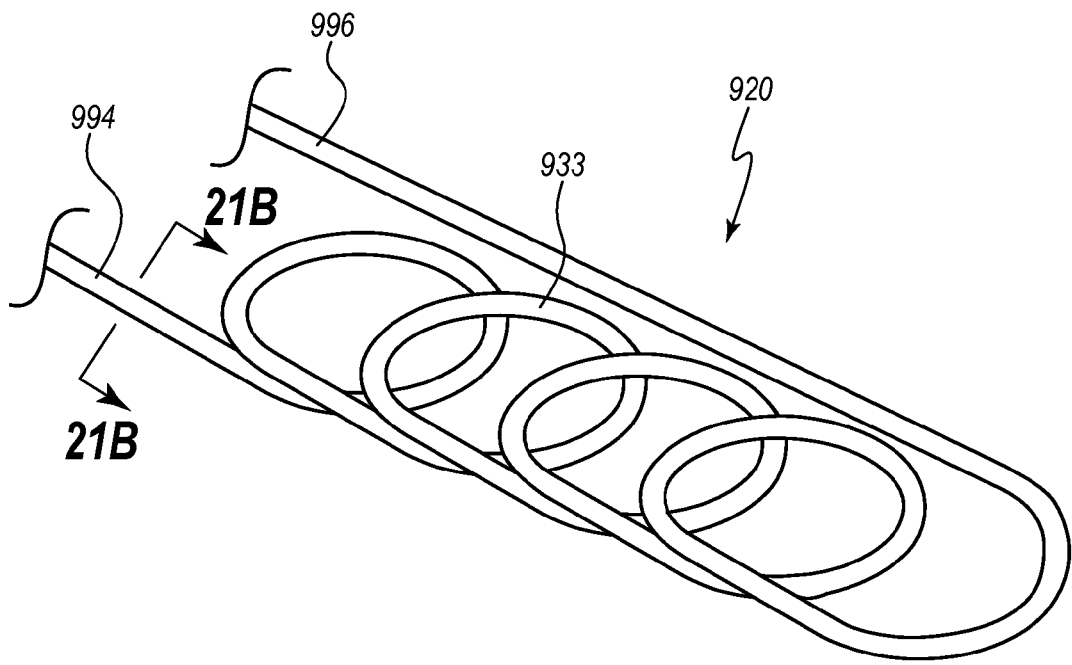
FIG. 21A is a perspective view of another embodiment of a heat sensor.
Figure 21B:
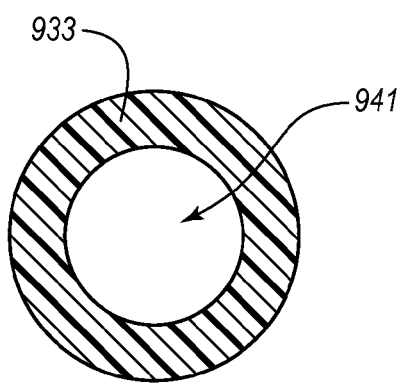
FIG. 21B is a cross-sectional view of the heat sensor of FIG. 21A taken along the view line 21B-21B in FIG. 21A.

As shown in FIG. 21B, the conduit 933 can define a fluid passageway or channel 941. The fluid channel 941 may be sufficiently large to permit ready passage of the guidewire 975 through it. The fluid channel 941 may additionally or alternatively be used to transport heat transfer fluid (such as the heat transfer fluid 161 discussed above). In some embodiments, the heat transfer fluid can flow through the fluid channel 941 and drain into the esophagus 60 at a distal end of the fluid channel 941. In the illustrated embodiment, the heat transfer fluid is cycled through the esophagus but is collected at an exterior of the patient.

As previously mentioned, while the drawings and written description have focused on illustrative devices, systems, and methods related to AF ablation procedures, it is to be understood that embodiments may be used in any other suitable context. Moreover, it will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 (f). Embodiments of the invention in which an exclusive property or privilege is claimed are defined as follows.

The invention claimed is:

1. A heat sensing assembly comprising:
a support structure that is configured to extend in a longitudinal direction when positioned within an anatomical vessel of a patient, the support structure having a natural configuration to which the support structure is biased to return when the support structure is displaced from the natural configuration, wherein the support structure is configured to be displaced from the natural configuration when positioned within the anatomical vessel; and
a fluid passageway carried by the support structure and defining a heat sensing region that is configured to extend in the longitudinal direction and in one or more lateral directions that are transverse to the longitudinal direction when the heat sensing assembly is deployed within the anatomical vessel,
wherein a portion of the heat sensing assembly that includes the support structure and the fluid passageway is flexible about at least one axis,
wherein the support structure is configured to permit heat to pass through it to or from the fluid passageway to alter a temperature of a fluid positioned in the fluid passageway when the heat sensing assembly is deployed, and
wherein the heat sensing assembly is configured to detect when a change in heat occurs at only a portion of the heat sensing region.

2. The heat sensing assembly of claim 1, wherein the fluid passageway is configured to permit flow of heat transfer fluid therein when the heat sensing assembly is in use, and wherein the support structure is configured to permit heat from a wall of an anatomical vessel to pass through the support structure into the fluid passageway to be transferred away from the wall of the anatomical vessel via the heat transfer fluid when the heat sensing assembly is in use.

3. The heat sensing assembly of claim 1, wherein the support structure is substantially cylindrical when in the natural configuration.

4. The heat sensing assembly of claim 1, wherein contact between the support structure and the anatomical vessel is configured to be at least partially maintained via one or more of an adhesive or surface tension.

5. The heat sensing assembly of claim 1, wherein the support structure is configured to hold an inflation fluid, and wherein contact between the support structure and the anatomical vessel is configured to be maintained via pressure provided by the inflation fluid.

6. The heat sensing assembly of claim 1, wherein the support structure is in a packaged state with at least a portion thereof being folded, rolled, or compressed.

7. The heat sensing assembly of claim 6, further comprising a packaging sheath that is configured to maintain the support structure in the packaged state.

8. The heat sensing assembly of claim 6, wherein the support structure encompasses at least a portion of an inflation assembly that is configured to transition the support structure from the packaged state to a deployed state.

9. The heat sensing assembly of claim 1, wherein the support structure comprises a substrate and a superstrate that are joined to each other, and wherein the fluid passageway is positioned between the substrate and the superstrate.

10. The heat sensing assembly of claim 9, wherein the support structure comprises a groove that defines the fluid passageway.

11. The heat sensing assembly of claim 1, wherein the fluid passageway is defined by a tubular conduit.

12. The heat sensing assembly of claim 11, wherein the conduit is coupled to a substrate.

13. The heat sensing assembly of claim 11, wherein tubular conduit defines the support structure.

14. The heat sensing assembly of claim 1, wherein the support structure is compliant so as to conform to an inner surface of the anatomical vessel.

15. The heat sensing assembly of claim 1, further comprising an inlet conduit and an outlet conduit coupled to the fluid passageway, wherein the inlet and outlet conduits are configured to extend from the fluid passageway at an interior of the anatomical vessel to an exterior of the patient when the heat sensing assembly is deployed within the anatomical vessel.

16. The heat sensing assembly of claim 1, further comprising an expandable balloon and an evacuation lumen that are configured to collapse an inner surface of the anatomical vessel against the support structure.

17. The heat sensing assembly of claim 16, wherein the support structure is flat, and wherein the expandable balloon and the evacuation lumen are configured to collapse a portion of the inner surface of the anatomical vessel against opposing sides of the support structure.

18. The heat sensing assembly of claim 1, further comprising an outlet conduit coupled with the fluid passageway, wherein the outlet conduit is configured to permit a level of a heat-sensitive fluid to rise and fall therein such that a change in temperature along the fluid passageway can be detected.

19. A heat sensor comprising:
a support structure configured to define a tube that is elongated in a longitudinal direction when the support structure is positioned within an esophagus of a patient, wherein the support structure is sufficiently compliant so as to conform to an inner surface of the esophagus;
a channel configured to receive a heat-sensitive fluid therein; and
an outlet conduit fluidly coupled with the channel, wherein the outlet conduit is configured to permit a level of the heat-sensitive fluid to rise and fall therein such that a change in heat within the plurality of channels can be detected.

20. The heat sensor of claim 19, wherein the support structure comprises an inner layer and an outer layer of a flexible material, and wherein the channel is positioned between the inner and outer layers.

21. The heat sensor of claim 19, further comprising an inlet conduit fluidly coupled with the channel, wherein the inlet conduit is configured to permit the heat-sensitive fluid to be selectively introduced into the channel.

22. A method of detecting heat changes of the esophagus during an ablative procedure of the heart, the method comprising:
positioning a heat sensor that comprises a fluid passageway that defines a heat sensing region within the esophagus such that the heat sensing region is maintained in proximity to an inner surface of the esophagus;
flowing heat transfer fluid through the fluid passageway;
measuring a change in a temperature of the heat transfer fluid after the heat transfer fluid has been conducted through at least a portion of the fluid passageway; and
cooling or heating the esophagus with the heat transfer fluid.

23. The method of claim 22, further comprising activating an alarm if the change in the temperature of the heat transfer fluid exceeds the threshold value.

24. The method of claim 22, further comprising automatically discontinuing ablation of the heart if the change in the temperature of the heat transfer fluid exceeds the threshold value.

* * * * *